(12) United States Patent
Rheinheimer et al.

(10) Patent No.: US 6,476,061 B1
(45) Date of Patent: Nov. 5, 2002

(54) FUNGICIDES CONTAINING PYRROLIDONES AS THEIR ACTIVE AGENTS

(75) Inventors: Joachim Rheinheimer, Ludwigshafen; Karl Eicken, Wachenheim; Ingo Rose, Mannheim; Thomas Grote, Schifferstadt; Eberhard Ammermann, Heppenheim; Gisela Lorenz, Neustadt; Siegfried Strathmann, Limburgerhof; Gerhard Hamprecht, Weinheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/831,406
(22) PCT Filed: Nov. 12, 1999
(86) PCT No.: PCT/EP99/08739
§ 371 (c)(1), (2), (4) Date: May 9, 2001
(87) PCT Pub. No.: WO00/30445
PCT Pub. Date: Jun. 2, 2000

(30) Foreign Application Priority Data

Nov. 24, 1998 (DE) .......................... 198 54 248

(51) Int. Cl.$^7$ .................... A61N 43/36; C07D 207/50
(52) U.S. Cl. ........................ 514/423; 548/530
(58) Field of Search ............. 514/423; 548/530

(56) References Cited

U.S. PATENT DOCUMENTS 4,582,849 A 4/1986 Marzolph

FOREIGN PATENT DOCUMENTS

DE 32 22 152 12/1983

OTHER PUBLICATIONS

Naik, et al, 1987, Med. Sci. Res., CAS–online abstract, 15(1), 27–8.*
Augustin, Et Al., Z.Chem., 13, Jg. (1973), pp. 214–216, XP–000901338.

* cited by examiner

*Primary Examiner*—Joseph K. McKane
*Assistant Examiner*—Andrea D. Small
(74) *Attorney, Agent, or Firm*—Keil & Weinkauf

(57) ABSTRACT

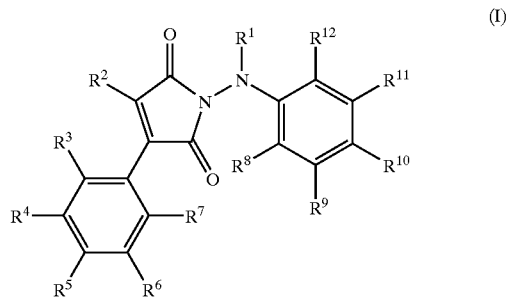

The invention relates to fungicides containing compounds of formula (I) as their active agents, the radicals in said formula (I) having the following meanings: $R^1$ is hydrogen, $C_1$–$C_6$-alkyl, $C_1$–$C_6$-alkylcarbonyl, formyl or $C_1$–$C_6$-halogenalkylcarbonyl; $R^2$ is hydrogen, $C_1$–$C_6$-alkyl or $C_1$–$C_6$-halogenalkyl; $R^3$–$R^{12}$ are hydrogen, halogen, $C_1$–$C_8$-cycloalkyl, $C_1$–$C_6$-alkyl, $C_1$–$C_6$-halogenalkyl, $C_1$–$C_6$-alkoxy, $C_1$–$C_6$-halogenalkoxy, $C_1$–$C_6$-alkylsulfonyl, $C_1$–$C_6$-halogenalkylsulfonyl, formyl, cyano, $C_1$–$C_6$-alkylthio or phenyl which can optionally be substituted by halogen atoms, $C_1$–$C_6$-alkyl or $C_1$–$C_6$-halogenalkyl groups, and to their agriculturally usable salts. The invention also relates to methods for combating fungi in plants using these fungicides.

18 Claims, No Drawings

FUNGICIDES CONTAINING PYRROLIDONES AS THEIR ACTIVE AGENTS

This application is a 371 of PCT/EP99/08379 Nov. 12, 1999.

The present invention relates to novel agrochemical compositions having fungicidal action comprising pyrrolidones as active compounds, and to their use in the treatment of plants and in agriculture.

The present invention provides compositions comprising as active compounds compounds of the formula I

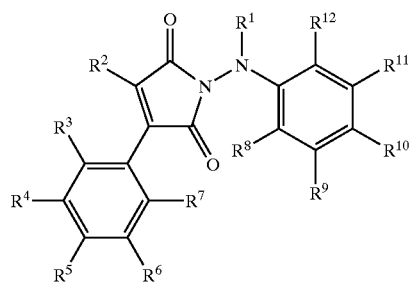

where:
$R^1$ is hydrogen, $C_1$–$C_6$-alkyl, $C_1$–$C_6$-alkylcarbonyl, formyl or $C_1$–$C_6$-haloalkylcarbonyl;
$R^2$ is hydrogen, $C_1$–$C_6$-alkyl or $C_1$–$C_6$-haloalkyl;
$R^3$–$R^{12}$ are hydrogen, halogen, $C_1$–$C_6$-cycloalkyl, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylsulfonyl, $C_1$–$C_6$-haloalkylsulfonyl, formyl, $C_1$–$C_6$-alkylcarbonyl, cyano, $C_1$–$C_6$-alkylthio or phenyl, which may be unsubstituted or substituted by halogen atoms, $C_1$–$C_6$-alkyl or $C_1$–$C_6$-haloalkyl groups, and their agriculturally useful salts.

Some of the compounds of the formula I are known from the literature (M. Augustin and P. Reinemann, Z. Chem. Volume 13, pp. 214–216 (1973), and/or they are commercially available. These are the following compounds:

1-anilino-3-phenylpyrrole-2,5-dione, 1-anilino-3-p-tolylpyrrole-2,5-dione, 1-(N-methylanilino)-3-p-tolylpyrrole-2,5-dione, 1-anilino-3-(3-chlorophenyl)pyrrole-2,5-dione, 1-anilino-3-(4-chlorophenyl)pyrrole-2,5-dione, 1-anilino-3-(4-bromophenyl)pyrrole-2,5-dione, 3-(4-chlorophenyl)-1-(N-methylanilino)pyrrole-2,5-dione, 1-(4-chloroanilino)-3-p-tolylpyrrole-2,5-dione, 3-(4-bromophenyl)-1-(4-methylanilino)pyrrole-2,5-dione, 1-(4-chloroanilino)-3-(4-chlorophenyl)pyrrole-2,5-dione, 1-anilino-3-(3,4-dichlorophenyl)pyrrole-2,5-dione, 3-(4-bromophenyl)-1-(4-methoxyanilino)pyrrole-2,5-dione, 3-(4-chlorophenyl)-1-(3,4-dichloroanilino)pyrrole-2,5-dione, 3-(4-methoxyphenyl)-1-(N-methylanilino)pyrrole-2,5-dione, 1-anilino-3-(4-methoxyphenyl)pyrrole-2,5-dione, 1-(4-chloroanilino)-3-(4-methoxyphenyl)pyrrole-2,5-dione, 1-(4-methoxyanilino)-3-(4-methoxyphenyl)pyrrole-2,5-dione, 1-(2-methoxyanilino)-3-(4-methoxyphenyl)pyrrole-2,5-dione, 1-(4-fluoroanilino)-3-(4-chlorophenyl)pyrrole-2,5-dione, 3-(4-chlorophenyl)-1-(4-methylanilino)pyrrole-2,5-dione, 1-(4-methylanilino)-3-phenylpyrrole-2,5-dione, 3-(4-chlorophenyl)-1-(2,4-dichloroanilino)pyrrole-2,5-dione, 1-(2,4-dichloroanilino)-3-phenylpyrrole-2,5-dione, 1-(2,4-dichloroanilino)-3-(4-methoxyphenyl)pyrrole-2,5-dione.

A fungicidal activity of these compounds has hitherto not been described.

Surprisingly, it has been found that compounds of the formula I have fungicidal activity. They are suitable for controlling harmful fungi in the treatment of plants, and also for the therapeutic treatment of diseases in humans caused by harmful fungi, and for veterinary treatment in mammals.

Compounds of the formula I can be prepared by the same method as that described in the literature (Z. Chem. Volume 13, pp. 214–216 (1973)). The starting materials are either known from the literature or commercially available.

In the definition of the substituents $R^1$ to $R^{12}$, the given terms are collective terms for a group of compounds.

In each case, halogen is fluorine, bromine, chlorine or iodine, in particular fluorine or chlorine.

Examples of other meanings are:
$C_1$–$C_6$-alkyl: methyl, ethyl, n-propyl, 1-methylethyl, n-butyl, 1-methylpropyl, 2-methylpropyl or 1,1-dimethylethyl, in particular ethyl;

$C_1$–$C_6$-haloalkyl: a $C_1$–$C_6$-alkyl radical as mentioned above such as partially or fully substituted by fluorine, chlorine, bromine and/or iodine, for example trichloromethyl, trifluoromethyl, 2-fluoroethyl, 2-chloroethyl, 2-bromoethyl, 2,2-difluoroethyl, 2,2,2-trifluoroethyl, 2,2,2-trichloroethyl, 2-fluoropropyl, 3-fluoropropyl, 2-chloropropyl or 3-chloropropyl, in particular 2-fluoroethyl or 2-chloroethyl;

$C_1$–$C_6$-alkoxy: methoxy, ethoxy, n-propoxy, 1-methylethoxy, n-butoxy, 1-methylpropoxy, 2-methylpropoxy or 1,1-dimethylethoxy, in particular methoxy or ethoxy;

$C_3$–$C_8$-cycloalkyl: for example cyclopropyl, cyclobutyl, cyclopentyl, cyclohexyl, cycloheptyl, cyclooctyl;

halo-$C_1$–$C_6$-alkoxy: a $C_1$–$C_6$-alkoxy radical as mentioned above which is substituted by fluorine, chlorine or bromine;

$C_1$–$C_6$-alkylcarbonyl: a carbonyl group which is substituted by a $C_1$–$C_6$-alkyl radical as mentioned above, such as, for example, acetyl, propionyl, butyryl;

halo-$C_1$–$C_6$-alkylcarbonyl: a $C_1$–$C_6$-alkylcarbonyl radical as mentioned above which is substituted by fluorine, chlorine or bromine;

$C_1$–$C_6$-alkylsulfonyl: a sulfonyl group which is substituted by a $C_1$–$C_6$-alkyl radical as mentioned above;

halo-$C_1$–$C_6$-alkylsulfonyl: a $C_1$–$C_6$-alkylsulfonyl radical as mentioned above which is substituted by fluorine, chlorine or bromine;

$C_1$–$C_6$-alkylthio: a sulfur atom which is substituted by a $C_1$–$C_6$-alkyl radical as mentioned above;

an unsubstituted or substituted phenyl radical: a phenyl radical which is mono- or polysubstituted. The substituents can be chosen at will, for example the following: halogen atoms, $C_1$–$C_6$-alkyl or halo-$C_1$–$C_6$-alkyl.

For the purpose of the present invention, the compounds listed under items 1–4 below are preferred with a view to the definitions of substituents mentioned, in each case on their own or in combination with one another:

1. Compounds of the formula 1, where $R^1$ is as defined below: hydrogen, methyl, ethyl or formyl, in particular hydrogen or methyl.
2. Compounds according to 1, where $R^2$ is as defined below: hydrogen, methyl, ethyl, trifluoromethyl, in particular hydrogen.

3. Compounds according to 1 or 2, where $R^3$–$R^{12}$ are as defined below: hydrogen, fluorine, chlorine, methyl, ethyl, propyl, butyl, trifluoromethyl, difluoromethyl, trifluoromethoxy, difluoromethoxy, methoxy, methylthio, cyano.

4. Compounds according to 1 to 3, where at least two of the radicals $R^8$–$R^{12}$ and in addition at least two of the radicals $R^3$–$R^7$ are hydrogen and the others are hydrogen, fluorine, chlorine, methyl, ethyl, propyl, butyl, trifluoromethyl, trifluoromethoxy or difluoromethoxy.

The two phenyl rings are preferably unsubstituted ($R^3$–$R^{12}$ =H) or preferably mono-, di- or trisubstituted, suitable substituents being mainly the following: $C_1$–$C_6$-alkyl, halogen, halo-$C_1$–$C_6$-alkyl, halo-$C_1$–$C_6$-alkoxy, in particular methyl, isopropyl, fluorine, chlorine, trifluoromethyl or trifluoromethoxy.

In general, the abovementioned compounds have been found to be particularly effective.

For the purpose of the present invention, for example the following compounds in Table 1 are suitable fungicidally active compounds:

TABLE 1

| No. | $R^1$ | $R^2$ | $R^3$ | $R^4$ | Phys. Data |
|---|---|---|---|---|---|
| 1) | H | H | phenyl | phenyl | |
| 2) | H | H | phenyl | 4-methylphenyl | |
| 3) | H | H | phenyl | 2,4-dichlorophenyl | |
| 4) | H | H | 4-methylphenyl | phenyl | |
| 5) | H | H | 4-methylphenyl | 4-chlorophenyl | |
| 6) | H | H | 4-methoxyphenyl | phenyl | |
| 7) | H | H | 4-methoxyphenyl | 4-methoxyphenyl | |
| 8) | H | H | 4-methoxyphenyl | 2-methoxyphenyl | |
| 9) | H | H | 4-methoxyphenyl | 4-chlorophenyl | |
| 10) | H | H | 4-methoxyphenyl | 2,4-dichlorophenyl | |
| 11) | H | H | 3-chlorophenyl | phenyl | |
| 12) | H | H | 3,4-dichlorophenyl | phenyl | m.p. 208–210° C. |
| 13) | H | H | 4-chlorophenyl | phenyl | |
| 14) | H | H | 4-chlorophenyl | 4-chlorophenyl | m.p. 192–193° C. |
| 15) | H | H | 4-Chlorophenyl | 3,4-dichlorophenyl | |
| 16) | H | H | 4-chlorophenyl | 2,4-dichlorophenyl | |
| 17) | H | H | 4-chlorophenyl | 4-fluorophenyl | |
| 18) | H | H | 4-chlorophenyl | 4-methylphenyl | |
| 19) | H | H | 4-bromophenyl | 4-methoxyphenyl | |
| 20) | H | H | 4-bromophenyl | 4-methylphenyl | |
| 21) | Methyl | H | 4-methylphenyl | phenyl | |
| 22) | Methyl | H | 4-methoxyphenyl | phenyl | |
| 23) | Methyl | H | 4-chlorophenyl | phenyl | m.p. 149–150° C. |
| 24) | Acetyl | H | phenyl | phenyl | |
| 25) | Trifluoroacetyl | H | phenyl | phenyl | |
| 26) | H | H | phenyl | 4-isopropylphenyl | 1H-NMR (DMSO-$d_6$): δ = 1.15 (d); 2.78 (m); 6.65 (d); 7.05 (d); 7.40 (s); 7.57 (m); 8.05 (m); 8.30 (s). |
| 27) | H | H | phenyl | 4-fluorophenyl | |
| 28) | H | H | phenyl | 3-fluorophenyl | |
| 29) | H | H | phenyl | 2-fluorophenyl | |
| 30) | H | H | phenyl | 2,3,5,6-tetrafluorophenyl | m.p. 123–125° C. |
| 31) | H | H | phenyl | 4-trifluoromethylphenyl | m.p. 211–214° C. |
| 32) | H | H | phenyl | 3-trifluoromethylphenyl | |
| 33) | H | H | phenyl | 4-methylsulphonylphenyl | m.p. 168–170° C. |
| 34) | H | H | phenyl | 4-chlorophenyl | m.p. 175–177° C. |
| 35) | H | H | phenyl | 3-chlorophenyl | m.p. 192–194° C. |
| 36) | H | H | phenyl | 2-chlorophenyl | m.p. 175–177° C. |
| 37) | H | H | phenyl | 3,5-dichlorophenyl | m.p. 234–236° C. |
| 38) | H | H | phenyl | 4-(trifluoromethoxy)phenyl | m.p. 174–176° C. |
| 39) | H | H | phenyl | 3-(trifluoromethoxy)phenyl | |
| 40) | H | H | phenyl | 4-(difluoromethoxy)phenyl | |
| 41) | H | H | phenyl | 3-(difluoromethoxy)phenyl | |
| 42) | H | H | phenyl | 4-cyanophenyl | |
| 43) | H | H | 4-chlorophenyl | 4-trifluoromethylphenyl | m.p. 206–208° C. |
| 44) | H | H | 4-chlorophenyl | 3-trifluoromethylphenyl | |
| 45) | H | H | 4-chlorophenyl | 2-chlorophenyl | m.p. 185–187° C. |
| 46) | H | H | 4-chlorophenyl | 3-chlorophenyl | m.p. 178–180° C. |
| 47) | H | H | 4-chlorophenyl | 4-trifluoromethoxyphenyl | |
| 48) | H | H | 4-chlorophenyl | 3-trifluoromethoxyphenyl | |
| 49) | H | H | 4-chlorophenyl | 4-difluoromethoxyphenyl | |

TABLE 1-continued

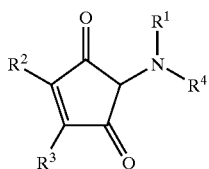

| No. | R¹ | R² | R³ | R⁴ | Phys. Data |
|---|---|---|---|---|---|
| 50) | H | H | 4-chlorophenyl | 3-difluoromethoxyphenyl | |
| 51) | H | H | 4-fluorophenyl | phenyl | m.p. 174–176° C. |
| 52) | H | H | 4-fluorophenyl | 4-ethylphenyl | |
| 53) | H | H | 4-fluorophenyl | 4-methylphenyl | |
| 54) | H | H | 4-fluorophenyl | 2-methylphenyl | |
| 55) | H | H | 4-fluorophenyl | 3-methylphenyl | |
| 56) | H | H | 4-fluorophenyl | 4-fluorophenyl | m.p. 183–186° C. |
| 57) | H | H | 4-fluorophenyl | 2,4-difluorophenyl | |
| 58) | H | H | 4-fluorophenyl | 4-chlorophenyl | |
| 59) | H | H | 4-fluorophenyl | 3-chlorophenyl | |
| 60) | H | H | 4-fluorophenyl | 2-chlorophenyl | |
| 61) | H | H | 4-fluorophenyl | 4-chloro-2-methoxyphenyl | |
| 62) | H | H | 4-fluorophenyl | 4-trifluoromethylphenyl | |
| 63) | H | H | 4-fluorophenyl | 2-trifluoromethylphenyl | |
| 64) | H | H | 4-fluorophenyl | 3-trifluoromethylphenyl | |
| 65) | H | H | 4-fluorophenyl | 4-(trifluoromethoxy)phenyl | |
| 66) | H | H | 4-fluorophenyl | 3-(trifluoromethoxy)phenyl | |
| 67) | H | H | 4-fluorophenyl | 4-(difluoromethoxy)phenyl | |
| 68) | H | H | 4-fluorophenyl | 3-(difluoromethoxy)phenyl | |
| 69) | H | H | 4-fluorophenyl | 4-cyanophenyl | |
| 70) | H | H | 3-fluorophenyl | phenyl | |
| 71) | H | H | 3-fluorophenyl | 4-ethylphenyl | |
| 72) | H | H | 3-fluorophenyl | 4-methylphenyl | |
| 73) | H | H | 3-fluorophenyl | 2-methylphenyl | |
| 74) | H | H | 3-fluorophenyl | 3-methylphenyl | |
| 75) | H | H | 3-fluorophenyl | 4-fluorophenyl | |
| 76) | H | H | 3-fluorophenyl | 2,4-difluorophenyl | |
| 77) | H | H | 3-fluorophenyl | 4-chlorophenyl | |
| 78) | H | H | 3-fluorophenyl | 3-chlorophenyl | |
| 79) | H | H | 3-fluorophenyl | 2-chlorophenyl | |
| 80) | H | H | 3-fluorophenyl | 4-chloro-2-methoxyphenyl | |
| 81) | H | H | 3-fluorophenyl | 4-trifluoromethylphenyl | |
| 82) | H | H | 3-fluorophenyl | 2-trifluoromethylphenyl | |
| 83) | H | H | 3-fluorophenyl | 3-trifluoromethylphenyl | |
| 84) | H | H | 3-fluorophenyl | 4-(trifluoromethoxy)phenyl | |
| 85) | H | H | 3-fluorophenyl | 3-(trifluoromethoxy)phenyl | |
| 86) | H | H | 3-fluorophenyl | 4-(difluoromethoxy)phenyl | |
| 87) | H | H | 3-fluorophenyl | 3-(difluoromethoxy)phenyl | |
| 88) | H | H | 3-fluorophenyl | 4-cyanophenyl | |
| 89) | H | H | 2-fluorophenyl | phenyl | |
| 90) | H | H | 2-fluorophenyl | 4-ethylphenyl | |
| 91) | H | H | 2-fluorophenyl | 4-methylphenyl | |
| 92) | H | H | 2-fluorophenyl | 2-methylphenyl | |
| 93) | H | H | 2-fluorophenyl | 3-methylphenyl | |
| 94) | H | H | 2-fluorophenyl | 4-fluorophenyl | |
| 95) | H | H | 2-fluorophenyl | 2,4-difluorophenyl | |
| 96) | H | H | 2-fluorophenyl | 4-chlorophenyl | |
| 97) | H | H | 2-fluorophenyl | 3-chlorophenyl | |
| 98) | H | H | 2-fluorophenyl | 2-chlorophenyl | |
| 99) | H | H | 2-fluorophenyl | 4-chloro-2-methoxyphenyl | |
| 100) | H | H | 2-fluorophenyl | 4-trifluoromethylphenyl | |
| 101) | H | H | 2-fluorophenyl | 2-trifluoromethylphenyl | |
| 102) | H | H | 2-fluorophenyl | 3-trifluoromethylphenyl | |
| 103) | H | H | 2-fluorophenyl | 4-(trifluoromethoxy)phenyl | |
| 104) | H | H | 2-fluorophenyl | 3-(trifluoromethoxy)phenyl | |
| 105) | H | H | 2-fluorophenyl | 4-(difluoromethoxy)phenyl | |
| 106) | H | H | 2-fluorophenyl | 3-(difluoromethoxy)phenyl | |
| 107) | H | H | 2-fluorophenyl | 4-cyanophenyl | |
| 108) | H | H | 2,4-difluorophenyl | phenyl | |
| 109) | H | H | 2,4-difluorophenyl | 4-ethylphenyl | |
| 110) | H | H | 2,4-difluorophenyl | 4-methylphenyl | |
| 111) | H | H | 2,4-difluorophenyl | 2-methylphenyl | |
| 112) | H | H | 2,4-difluorophenyl | 3-methylphenyl | |
| 113) | H | H | 2,4-difluorophenyl | 4-fluorophenyl | |
| 114) | H | H | 2,4-difluorophenyl | 2,4-difluorophenyl | |
| 115) | H | H | 2,4-difluorophenyl | 4-chlorophenyl | |
| 116) | H | H | 2,4-difluorophenyl | 3-chlorophenyl | |
| 117) | H | H | 2,4-difluorophenyl | 2-chlorophenyl | |
| 118) | H | H | 2,4-difluorophenyl | 4-chloro-2-methoxyphenyl | |
| 119) | H | H | 2,4-difluorophenyl | 4-trifluoromethylphenyl | |
| 120) | H | H | 2,4-difluorophenyl | 2-trifluoromethylphenyl | |
| 121) | H | H | 2,4-difluorophenyl | 3-trifluoromethylphenyl | |
| 122) | H | H | 2,4-difluorophenyl | 4-(trifluoromethoxy)phenyl | |
| 123) | H | H | 2,4-difluorophenyl | 3-(trifluoromethoxy)phenyl | |
| 124) | H | H | 2,4-difluorophenyl | 4-(difluoromethoxy)phenyl | |
| 125) | H | H | 2,4-difluorophenyl | 3-(difluoromethoxy)phenyl | |
| 126) | H | H | 2,4-difluorophenyl | 4-cyanophenyl | |
| 127) | H | H | 4-trifluoromethylphenyl | phenyl | |
| 128) | H | H | 4-trifluoromethylphenyl | 4-ethylphenyl | |
| 129) | H | H | 4-trifluoromethylphenyl | 4-methylphenyl | |

TABLE 1-continued

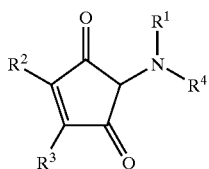

| No. | R¹ | R² | R³ | R⁴ | Phys. Data |
|---|---|---|---|---|---|
| 130) | H | H | 4-trifluoromethylphenyl | 2-methylphenyl | |
| 131) | H | H | 4-trifluoromethylphenyl | 3-methylphenyl | |
| 132) | H | H | 4-trifluoromethylphenyl | 4-fluorophenyl | |
| 133) | H | H | 4-trifluoromethylphenyl | 2,4-difluorophenyl | |
| 134) | H | H | 4-trifluoromethylphenyl | 4-chlorophenyl | |
| 135) | H | H | 4-trifluoromethylphenyl | 3-chlorophenyl | |
| 136) | H | H | 4-trifluoromethylphenyl | 2-chlorophenyl | |
| 137) | H | H | 4-trifluoromethylphenyl | 4-chloro-2-methoxyphenyl | |
| 138) | H | H | 4-trifluoromethylphenyl | 4-trifluoromethylphenyl | |
| 139) | H | H | 4-trifluoromethylphenyl | 2-trifluoromethylphenyl | |
| 140) | H | H | 4-trifluoromethylphenyl | 3-trifluoromethylphenyl | |
| 141) | H | H | 4-trifluoromethylphenyl | 4-(trifluoromethoxy)phenyl | |
| 142) | H | H | 4-trifluoromethylphenyl | 3-(trifluoromethoxy)phenyl | |
| 143) | H | H | 4-trifluoromethylphenyl | 4-(difluoromethoxy)phenyl | |
| 144) | H | H | 4-trifluoromethylphenyl | 3-(difluoromethoxy)phenyl | |
| 145) | H | H | 4-trifluoromethylphenyl | 4-cyanophenyl | |
| 146) | H | H | 3,4-dichlorophenyl | 4-fluorophenyl | 1H-NMR (DMSO-d₆): δ = 6.80 (m); 7.00 (t); 7.57 (s); 7.83 (d); 8.05 (d); 8.35 (s); 8.40 (s). m.p. 188–190° C. |
| 147) | H | H | 3,4-(methylenedioxy)phenyl | phenyl | |
| 148) | H | H | 3-trifluoromethylphenyl | phenyl | |
| 149) | H | H | 3-trifluoromethylphenyl | 4-ethylphenyl | |
| 150) | H | H | 3-trifluoromethylphenyl | 4-methylphenyl | |
| 151) | H | H | 3-trifluoromethylphenyl | 2-methylphenyl | |
| 152) | H | H | 3-trifluoromethylphenyl | 3-methylphenyl | |
| 153) | H | H | 3-trifluoromethylphenyl | 4-fluorophenyl | |
| 154) | H | H | 3-trifluoromethylphenyl | 2,4-difluorophenyl | |
| 155) | H | H | 3-trifluoromethylphenyl | 4-chlorophenyl | |
| 156) | H | H | 3-trifluoromethylphenyl | 3-chlorophenyl | |
| 157) | H | H | 3-trifluoromethylphenyl | 2-chlorophenyl | |
| 158) | H | H | 3-trifluoromethylphenyl | 4-chloro-2-methoxyphenyl | |

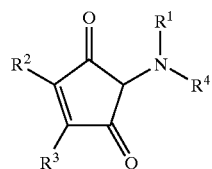

| No. | R¹ | R² | R³ | R⁴ | Phys. Data |
|---|---|---|---|---|---|
| 159) | H | H | 3-trifluoromethylphenyl | 4-trifluoromethylphenyl | |
| 160) | H | H | 3-trifluoromethylphenyl | 2-trifluoromethylphenyl | |
| 161) | H | H | 3-trifluoromethylphenyl | 3-trifluoromethylphenyl | |
| 162) | H | H | 3-trifluoromethylphenyl | 4-(trifluoromethoxy)phenyl | |
| 163) | H | H | 3-trifluoromethylphenyl | 3-(trifluoromethoxy)phenyl | |
| 164) | H | H | 3-trifluoromethylphenyl | 4-(difluoromethoxy)phenyl | |
| 165) | H | H | 3-trifluoromethylphenyl | 3-(difluoromethoxy)phenyl | |
| 166) | H | H | 3-trifluoromethylphenyl | 4-cyanophenyl | |
| 167) | methyl | H | phenyl | phenyl | 1H-NMR (CDCl₃): δ = 3.38 (s); 6.80 (m); 6.90 (t); 7.72 (m); 7.50 (m); 7.97 (m). |
| 168) | methyl | H | phenyl | 4-methylphenyl | |
| 169) | methyl | H | phenyl | 2,4-dichlorophenyl | |
| 170) | methyl | H | 4-methylphenyl | 4-chlorophenyl | |
| 171) | methyl | H | 4-methoxyphenyl | 4-methoxyphenyl | |
| 172) | methyl | H | 4-methoxyphenyl | 2-methoxyphenyl | |
| 173) | methyl | H | 4-methoxyphenyl | 4-chlorophenyl | |
| 174) | methyl | H | 4-methoxyphenyl | 2,4-dichlorophenyl | |
| 175) | methyl | H | 3-chlorophenyl | phenyl | |
| 176) | methyl | H | 3,4-dichlorophenyl | phenyl | |
| 177) | methyl | H | 4-chlorophenyl | 4-chlorophenyl | |
| 178) | methyl | H | 4-chlorophenyl | 3,4-dichlorophenyl | |
| 179) | methyl | H | 4-chlorophenyl | 2,4-dichlorophenyl | |
| 180) | methyl | H | 4-chlorophenyl | 4-fluorophenyl | |
| 181) | methyl | H | 4-chlorophenyl | 4-methylphenyl | |
| 182) | methyl | H | 4-bromophenyl | 4-methoxyphenyl | |
| 183) | methyl | H | 4-bromophenyl | 4-methylphenyl | |
| 184) | methyl | H | phenyl | 4-isopropylphenyl | |
| 185) | methyl | H | phenyl | 4-fluorophenyl | |
| 186) | methyl | H | phenyl | 3-fluorophenyl | |
| 187) | methyl | H | phenyl | 2-fluorophenyl | |
| 188) | methyl | H | phenyl | 2,3,5,6-tetrafluorophenyl | |
| 189) | methyl | H | phenyl | 4-trifluoromethylphenyl | |
| 190) | methyl | H | phenyl | 3-trifluoromethylphenyl | |
| 191) | methyl | H | phenyl | 4-methylsulfonylphenyl | |
| 192) | methyl | H | phenyl | 4-chlorophenyl | |
| 193) | methyl | H | phenyl | 3-chlorophenyl | |
| 194) | methyl | H | phenyl | 2-chlorophenyl | |
| 195) | methyl | H | phenyl | 3,5-dichlorophenyl | |

TABLE 1-continued

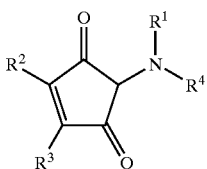

| No. | R¹ | R² | R³ | R⁴ | Phys. Data |
|---|---|---|---|---|---|
| 196) | methyl | H | phenyl | 4-(trifluoromethoxy)phenyl | |
| 197) | methyl | H | phenyl | 3-(trifluoromethoxy)phenyl | |
| 198) | methyl | H | phenyl | 4-(difluoromethoxy)phenyl | |
| 199) | methyl | H | phenyl | 3-(difluoromethoxy)phenyl | |
| 200) | methyl | H | phenyl | 4-cyanophenyl | |
| 201) | methyl | H | 4-chlorophenyl | 4-trifluoromethylphenyl | |
| 202) | methyl | H | 4-chlorophenyl | 3-trifluoromethylphenyl | |
| 203) | methyl | H | 4-chlorophenyl | 2-chlorophenyl | |
| 204) | methyl | H | 4-chlorophenyl | 3-chlorophenyl | |
| 205) | methyl | H | 4-chlorophenyl | 4-trifluoromethoxyphenyl | |
| 206) | methyl | H | 4-chlorophenyl | 3-trifluoromethoxyphenyl | |
| 207) | methyl | H | 4-chlorophenyl | 4-difluoromethoxyphenyl | |
| 208) | methyl | H | 4-chlorophenyl | 3-difluoromethoxyphenyl | |
| 209) | methyl | H | 4-fluorophenyl | phenyl | |
| 210) | methyl | H | 4-fluorophenyl | 4-ethylphenyl | |
| 211) | methyl | H | 4-fluorophenyl | 4-methylphenyl | |
| 212) | methyl | H | 4-fluorophenyl | 2-methylphenyl | |
| 213) | methyl | H | 4-fluorophenyl | 3-methylphenyl | |
| 214) | methyl | H | 4-fluorophenyl | 4-fluorophenyl | |
| 215) | methyl | H | 4-fluorophenyl | 2,4-difluorophenyl | |
| 216) | methyl | H | 4-fluorophenyl | 4-chlorophenyl | |
| 217) | methyl | H | 4-fluorophenyl | 3-chlorophenyl | |
| 218) | methyl | H | 4-fluorophenyl | 2-chlorophenyl | |
| 219) | methyl | H | 4-fluorophenyl | 4-chloro-2-methoxyphenyl | |
| 220) | methyl | H | 4-fluorophenyl | 4-trifluoromethylphenyl | |
| 221) | methyl | H | 4-fluorophenyl | 2-trifluoromethylphenyl | |
| 222) | methyl | H | 4-fluorophenyl | 3-trifluoromethylphenyl | |
| 223) | methyl | H | 4-fluorophenyl | 4-(trifluoromethoxy)phenyl | |
| 224) | methyl | H | 4-fluorophenyl | 3-(trifluoromethoxy)phenyl | |
| 225) | methyl | H | 4-fluorophenyl | 4-(difluoromethoxy)phenyl | |
| 226) | methyl | H | 4-fluorophenyl | 3-(difluoromethoxy)phenyl | |
| 227) | methyl | H | 4-fluorophenyl | 4-cyanophenyl | |
| 228) | methyl | H | 3-fluorophenyl | phenyl | |
| 229) | methyl | H | 3-fluorophenyl | 4-ethylphenyl | |
| 230) | methyl | H | 3-fluorophenyl | 4-methylphenyl | |
| 231) | methyl | H | 3-fluorophenyl | 2-methylphenyl | |
| 232) | methyl | H | 3-fluorophenyl | 3-methylphenyl | |
| 233) | methyl | H | 3-fluorophenyl | 4-fluorophenyl | |
| 234) | methyl | H | 3-fluorophenyl | 2,4-difluorophenyl | |
| 235) | methyl | H | 3-fluorophenyl | 4-chlorophenyl | |
| 236) | methyl | H | 3-fluorophenyl | 3-chlorophenyl | |
| 237) | methyl | H | 3-fluorophenyl | 2-chlorophenyl | |
| 238) | methyl | H | 3-fluorophenyl | 4-chloro-2-methoxyphenyl | |
| 239) | methyl | H | 3-fluorophenyl | 4-trifluoromethylphenyl | |
| 240) | methyl | H | 3-fluorophenyl | 2-trifluoromethylphenyl | |
| 241) | methyl | H | 3-fluorophenyl | 3-trifluoromethylphenyl | |
| 242) | methyl | H | 3-fluorophenyl | 4-(trifluoromethoxy)phenyl | |
| 243) | methyl | H | 3-fluorophenyl | 3-(trifluoromethoxy)phenyl | |
| 244) | methyl | H | 3-fluorophenyl | 4-(difluoromethoxy)phenyl | |
| 245) | methyl | H | 3-fluorophenyl | 3-(difluoromethoxy)phenyl | |
| 246) | methyl | H | 3-fluorophenyl | 4-cyanophenyl | |
| 247) | methyl | H | 2-fluorophenyl | phenyl | |
| 248) | methyl | H | 2-fluorophenyl | 4-ethylphenyl | |
| 249) | methyl | H | 2-fluorophenyl | 4-methylphenyl | |
| 250) | methyl | H | 2-fluorophenyl | 2-methylphenyl | |
| 251) | methyl | H | 2-fluorophenyl | 3-methylphenyl | |
| 252) | methyl | H | 2-fluorophenyl | 4-fluorophenyl | |
| 253) | methyl | H | 2-fluorophenyl | 2,4-difluorophenyl | |
| 254) | methyl | H | 2-fluorophenyl | 4-chlorophenyl | |
| 255) | methyl | H | 2-fluorophenyl | 3-chlorophenyl | |
| 256) | methyl | H | 2-fluorophenyl | 2-chlorophenyl | |
| 257) | methyl | H | 2-fluorophenyl | 4-chloro-2-methoxyphenyl | |
| 258) | methyl | H | 2-fluorophenyl | 4-trifluoromethylphenyl | |
| 259) | methyl | H | 2-fluorophenyl | 2-trifluoromethylphenyl | |
| 260) | methyl | H | 2-fluorophenyl | 3-trifluoromethylphenyl | |
| 261) | methyl | H | 2-fluorophenyl | 4-(trifluoromethoxy)phenyl | |
| 262) | methyl | H | 2-fluorophenyl | 3-(trifluoromethoxy)phenyl | |
| 263) | methyl | H | 2-fluorophenyl | 4-(difluoromethoxy)phenyl | |
| 264) | methyl | H | 2-fluorophenyl | 3-(difluoromethoxy)phenyl | |
| 265) | methyl | H | 2-fluorophenyl | 4-cyanophenyl | |
| 266) | methyl | H | 2,4-difluorophenyl | phenyl | |
| 267) | methyl | H | 2,4-difluorophenyl | 4-ethylphenyl | |
| 268) | methyl | H | 2,4-difluorophenyl | 4-methylphenyl | |
| 269) | methyl | H | 2,4-difluorophenyl | 2-methylphenyl | |
| 270) | methyl | H | 2,4-difluorophenyl | 3-methylphenyl | |
| 271) | methyl | H | 2,4-difluorophenyl | 4-fluorophenyl | |
| 272) | methyl | H | 2,4-difluorophenyl | 2,4-difluorophenyl | |
| 273) | methyl | H | 2,4-difluorophenyl | 4-chlorophenyl | |
| 274) | methyl | H | 2,4-difluorophenyl | 3-chlorophenyl | |
| 275) | methyl | H | 2,4-difluorophenyl | 2-chlorophenyl | |
| 276) | methyl | H | 2,4-difluorophenyl | 4-chloro-2-methoxyphenyl | |
| 277) | methyl | H | 2,4-difluorophenyl | 4-trifluoromethylphenyl | |
| 278) | methyl | H | 2,4-difluorophenyl | 2-trifluoromethylphenyl | |

TABLE 1-continued

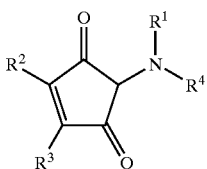

| No. | R¹ | R² | R³ | R⁴ | Phys. Data |
|---|---|---|---|---|---|
| 279) | methyl | H | 2,4-difluorophenyl | 3-trifluoromethylphenyl | |
| 280) | methyl | H | 2,4-difluorophenyl | 4-(trifluoromethoxy)phenyl | |
| 281) | methyl | H | 2,4-difluorophenyl | 3-(trifluoromethoxy)phenyl | |
| 282) | methyl | H | 2,4-difluorophenyl | 4-(difluoromethoxy)phenyl | |
| 283) | methyl | H | 2,4-difluorophenyl | 3-(difluoromethoxy)phenyl | |
| 284) | methyl | H | 2,4-difluorophenyl | 4-cyanophenyl | |
| 285) | methyl | H | 4-trifluoromethylphenyl | phenyl | |
| 286) | methyl | H | 4-trifluoromethylphenyl | 4-ethylphenyl | |
| 287) | methyl | H | 4-trifluoromethylphenyl | 4-methylphenyl | |
| 288) | methyl | H | 4-trifluoromethylphenyl | 2-methylphenyl | |
| 289) | methyl | H | 4-trifluoromethylphenyl | 3-methylphenyl | |
| 290) | methyl | H | 4-trifluoromethylphenyl | 4-fluorophenyl | |
| 291) | methyl | H | 4-trifluoromethylphenyl | 2,4-difluorophenyl | |
| 292) | methyl | H | 4-trifluoromethylphenyl | 4-chlorophenyl | |
| 293) | methyl | H | 4-trifluoromethylphenyl | 3-chlorophenyl | |
| 294) | methyl | H | 4-trifluoromethylphenyl | 2-chlorophenyl | |
| 295) | methyl | H | 4-trifluoromethylphenyl | 4-chloro-2-methoxyphenyl | |
| 296) | methyl | H | 4-trifluoromethylphenyl | 4-trifluoromethylphenyl | |
| 297) | methyl | H | 4-trifluoromethylphenyl | 2-trifluoromethylphenyl | |
| 298) | methyl | H | 4-trifluoromethylphenyl | 3-trifluoromethylphenyl | |
| 299) | methyl | H | 4-trifluoromethylphenyl | 4-(trifluoromethoxy)phenyl | |
| 300) | methyl | H | 4-trifluoromethylphenyl | 3-(trifluoromethoxy)phenyl | |
| 301) | methyl | H | 4-trifluoromethylphenyl | 4-(difluoromethoxy)phenyl | |
| 302) | methyl | H | 4-trifluoromethylphenyl | 3-(difluoromethoxy)phenyl | |
| 303) | methyl | H | 4-trifluoromethylphenyl | 4-cyanophenyl | |
| 304) | methyl | H | 3,4-dichlorophenyl | 4-fluorophenyl | |
| 305) | methyl | H | 3,4-(methylenedioxy)phenyl | phenyl | |
| 306) | methyl | H | 3-trifluoromethylphenyl | phenyl | |
| 307) | methyl | H | 3-trifluoromethylphenyl | 4-ethylphenyl | |
| 308) | methyl | H | 3-trifluoromethylphenyl | 4-methylphenyl | |
| 309) | methyl | H | 3-trifluoromethylphenyl | 2-methylphenyl | |
| 310) | methyl | H | 3-trifluoromethylphenyl | 3-methylphenyl | |
| 311) | methyl | H | 3-trifluoromethylphenyl | 4-fluorophenyl | |
| 312) | methyl | H | 3-trifluoromethylphenyl | 2,4-difluorophenyl | |
| 313) | methyl | H | 3-trifluoromethylphenyl | 4-chlorophenyl | |
| 314) | methyl | H | 3-trifluoromethylphenyl | 3-chlorophenyl | |
| 315) | methyl | H | 3-trifluoromethylphenyl | 2-chlorophenyl | |
| 316) | methyl | H | 3-trifluoromethylphenyl | 4-chloro-2-methoxyphenyl | |
| 317) | methyl | H | 3-trifluoromethylphenyl | 4-trifluoromethylphenyl | |
| 318) | methyl | H | 3-trifluoromethylphenyl | 2-trifluoromethylphenyl | |
| 319) | methyl | H | 3-trifluoromethylphenyl | 3-trifluoromethylphenyl | |
| 320) | methyl | H | 3-trifluoromethylphenyl | 4-(trifluoromethoxy)phenyl | |
| 321) | methyl | H | 3-trifluoromethylphenyl | 3-(trifluoromethoxy)phenyl | |
| 322) | methyl | H | 3-trifluoromethylphenyl | 4-(difluoromethoxy)phenyl | |
| 323) | methyl | H | 3-trifluoromethylphenyl | 3-(difluoromethoxy)phenyl | |
| 324) | methyl | H | 3-trifluoromethylphenyl | 4-cyanophenyl | |
| 325) | formyl | H | phenyl | phenyl | |
| 326) | formyl | H | phenyl | 4-methylphenyl | |
| 327) | formyl | H | phenyl | 2,4-dichlorophenyl | |
| 328) | formyl | H | 4-methylphenyl | 4-chlorophenyl | |
| 329) | formyl | H | 4-methoxyphenyl | 4-methoxyphenyl | |
| 330) | formyl | H | 4-methoxyphenyl | 2-methoxyphenyl | |
| 331) | formyl | H | 4-methoxyphenyl | 4-chlorophenyl | |
| 332) | formyl | H | 4-methoxyphenyl | 2,4-dichlorophenyl | |
| 333) | formyl | H | 3-chlorophenyl | phenyl | |
| 334) | formyl | H | 3,4-dichlorophenyl | phenyl | |
| 335) | formyl | H | 4-chlorophenyl | 4-chlorophenyl | |
| 336) | formyl | H | 4-chlorophenyl | 3,4-dichlorophenyl | |
| 337) | formyl | H | 4-chlorophenyl | 2,4-dichlorophenyl | |
| 338) | formyl | H | 4-chlorophenyl | 4-fluorophenyl | |
| 339) | formyl | H | 4-chlorophenyl | 4-formylphenyl | |
| 340) | formyl | H | 4-bromophenyl | 4-methoxyphenyl | |
| 341) | formyl | H | 4-bromophenyl | 4-formylphenyl | |
| 342) | formyl | H | phenyl | 4-isopropylphenyl | |
| 343) | formyl | H | phenyl | 4-fluorophenyl | |
| 344) | formyl | H | phenyl | 3-fluorophenyl | |
| 345) | formyl | H | phenyl | 2-fluorophenyl | |
| 346) | formyl | H | phenyl | 2,3,5,6-tetrafluorophenyl | |
| 347) | formyl | H | phenyl | 4-trifluoromethylphenyl | |
| 348) | formyl | H | phenyl | 3-trifluoromethylphenyl | |
| 349) | formyl | H | phenyl | 4-formylsulfonylphenyl | |
| 350) | formyl | H | phenyl | 4-chlorophenyl | |
| 351) | formyl | H | phenyl | 3-chlorophenyl | |
| 352) | formyl | H | phenyl | 2-chlorophenyl | |

TABLE 1-continued

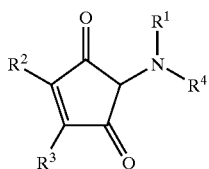

| No. | R¹ | R² | R³ | R⁴ | Phys. Data |
|---|---|---|---|---|---|
| 353) | formyl | H | phenyl | 3,5-dichlorophenyl | |
| 354) | formyl | H | phenyl | 4-(trifluoromethoxy)phenyl | |
| 355) | formyl | H | phenyl | 3-(trifluoromethoxy)phenyl | |
| 356) | formyl | H | phenyl | 4-(difluoromethoxy)phenyl | |
| 357) | formyl | H | phenyl | 3-(difluoromethoxy)phenyl | |
| 358) | formyl | H | phenyl | 4-cyanophenyl | |
| 359) | formyl | H | 4-chlorophenyl | 4-trifluoromethylphenyl | |
| 360) | formyl | H | 4-chlorophenyl | 3-trifluoromethylphenyl | |
| 361) | formyl | H | 4-chlorophenyl | 2-chlorophenyl | |
| 362) | formyl | H | 4-chlorophenyl | 3-chlorophenyl | |
| 363) | formyl | H | 4-chlorophenyl | 4-trifluoromethoxyphenyl | |
| 364) | formyl | H | 4-chlorophenyl | 3-trifluoromethoxyphenyl | |
| 365) | formyl | H | 4-chlorophenyl | 4-difluoromethoxyphenyl | |
| 366) | formyl | H | 4-chlorophenyl | 3-difluoromethoxyphenyl | |
| 367) | formyl | H | 4-fluorophenyl | phenyl | |
| 368) | formyl | H | 4-fluorophenyl | 4-ethylphenyl | |
| 369) | formyl | H | 4-fluorophenyl | 4-formylphenyl | |
| 370) | formyl | H | 4-fluorophenyl | 2-formylphenyl | |
| 371) | formyl | H | 4-fluorophenyl | 3-formylphenyl | |
| 372) | formyl | H | 4-fluorophenyl | 4-fluorophenyl | |
| 373) | formyl | H | 4-fluorophenyl | 2,4-difluorophenyl | |
| 374) | formyl | H | 4-fluorophenyl | 4-chlorophenyl | |
| 375) | formyl | H | 4-fluorophenyl | 3-chlorophenyl | |
| 376) | formyl | H | 4-fluorophenyl | 2-chlorophenyl | |
| 377) | formyl | H | 4-fluorophenyl | 4-chloro-2-methoxyphenyl | |
| 378) | formyl | H | 4-fluorophenyl | 4-trifluoromethylphenyl | |
| 379) | formyl | H | 4-fluorophenyl | 2-trifluoromethylphenyl | |
| 380) | formyl | H | 4-fluorophenyl | 3-trifluoromethylphenyl | |
| 381) | formyl | H | 4-fluorophenyl | 4-(trifluoromethoxy)phenyl | |
| 382) | formyl | H | 4-fluorophenyl | 3-(trifluoromethoxy)phenyl | |
| 383) | formyl | H | 4-fluorophenyl | 4-(difluoromethoxy)phenyl | |
| 384) | formyl | H | 4-fluorophenyl | 3-(difluoromethoxy)phenyl | |
| 385) | formyl | H | 4-fluorophenyl | 4-cyanophenyl | |
| 386) | formyl | H | 3-fluorophenyl | phenyl | |
| 387) | formyl | H | 3-fluorophenyl | 4-ethylphenyl | |
| 388) | formyl | H | 3-fluorophenyl | 4-formylphenyl | |
| 389) | formyl | H | 3-fluorophenyl | 2-formylphenyl | |
| 390) | formyl | H | 3-fluorophenyl | 3-formylphenyl | |
| 391) | formyl | H | 3-fluorophenyl | 4-fluorophenyl | |
| 392) | formyl | H | 3-fluorophenyl | 2,4-difluorophenyl | |
| 393) | formyl | H | 3-fluorophenyl | 4-chlorophenyl | |
| 394) | formyl | H | 3-fluorophenyl | 3-chlorophenyl | |
| 395) | formyl | H | 3-fluorophenyl | 2-chlorophenyl | |
| 396) | formyl | H | 3-fluorophenyl | 4-chloro-2-methoxyphenyl | |

TABLE 1-continued

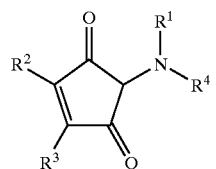

| No. | R¹ | R² | R³ | R⁴ | Phys. Data |
|---|---|---|---|---|---|
| 397) | formyl | H | 3-fluorophenyl | 4-trifluoromethylphenyl | |
| 398) | formyl | H | 3-fluorophenyl | 2-trifluoromethylphenyl | |
| 399) | formyl | H | 3-fluorophenyl | 3-trifluoromethylphenyl | |
| 400) | formyl | H | 3-fluorophenyl | 4-(trifluoromethoxy)phenyl | |
| 401) | formyl | H | 3-fluorophenyl | 3-(trifluoromethoxy)phenyl | |
| 402) | formyl | H | 3-fluorophenyl | 4-(difluoromethoxy)phenyl | |
| 403) | formyl | H | 3-fluorophenyl | 3-(difluoromethoxy)phenyl | |
| 404) | formyl | H | 3-fluorophenyl | 4-cyanophenyl | |
| 405) | formyl | H | 2-fluorophenyl | phenyl | |
| 406) | formyl | H | 2-fluorophenyl | 4-ethylphenyl | |
| 407) | formyl | H | 2-fluorophenyl | 4-formylphenyl | |
| 408) | formyl | H | 2-fluorophenyl | 2-formylphenyl | |
| 409) | formyl | H | 2-fluorophenyl | 3-formylphenyl | |
| 410) | formyl | H | 2-fluorophenyl | 4-fluorophenyl | |
| 411) | formyl | H | 2-fluorophenyl | 2,4-difluorophenyl | |
| 412) | formyl | H | 2-fluorophenyl | 4-chlorophenyl | |
| 413) | formyl | H | 2-fluorophenyl | 3-chlorophenyl | |
| 414) | formyl | H | 2-fluorophenyl | 2-chlorophenyl | |
| 415) | formyl | H | 2-fluorophenyl | 4-chloro-2-methoxyphenyl | |
| 416) | formyl | H | 2-fluorophenyl | 4-trifluoromethylphenyl | |
| 417) | formyl | H | 2-fluorophenyl | 2-trifluoromethylphenyl | |
| 418) | formyl | H | 2-fluorophenyl | 3-trifluoromethylphenyl | |
| 419) | formyl | H | 2-fluorophenyl | 4-(trifluoromethoxy)phenyl | |
| 420) | formyl | H | 2-fluorophenyl | 3-(trifluoromethoxy)phenyl | |
| 421) | formyl | H | 2-fluorophenyl | 4-(difluoromethoxy)phenyl | |
| 422) | formyl | H | 2-fluorophenyl | 3-(difluoromethoxy)phenyl | |
| 423) | formyl | H | 2-fluorophenyl | 4-cyanophenyl | |
| 424) | formyl | H | 2,4-difluorophenyl | phenyl | |
| 425) | formyl | H | 2,4-difluorophenyl | 4-ethylphenyl | |
| 426) | formyl | H | 2,4-difluorophenyl | 4-formylphenyl | |
| 427) | formyl | H | 2,4-difluorophenyl | 2-formylphenyl | |
| 428) | formyl | H | 2,4-difluorophenyl | 3-formylphenyl | |
| 429) | formyl | H | 2,4-difluorophenyl | 4-fluorophenyl | |
| 430) | formyl | H | 2,4-difluorophenyl | 2,4-difluorophenyl | |
| 431) | formyl | H | 2,4-difluorophenyl | 4-chlorophenyl | |
| 432) | formyl | H | 2,4-difluorophenyl | 3-chlorophenyl | |
| 433) | formyl | H | 2,4-difluorophenyl | 2-chlorophenyl | |
| 434) | formyl | H | 2,4-difluorophenyl | 4-chloro-2-methoxyphenyl | |
| 435) | formyl | H | 2,4-difluorophenyl | 4-trifluoromethylphenyl | |

TABLE 1-continued

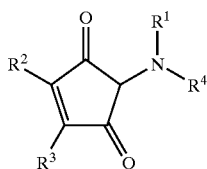

| No. | R¹ | R² | R³ | R⁴ | Phys. Data |
|---|---|---|---|---|---|
| 436) | formyl | H | 2,4-difluorophenyl | 2-trifluoromethylphenyl | |
| 437) | formyl | H | 2-4-difluorophenyl | 3-trifluoromethylphenyl | |
| 438) | formyl | H | 2,4-difluorophenyl | 4-(trifluoromethoxy)phenyl | |
| 439) | formyl | H | 2,4-difluorophenyl | 3-(trifluoromethoxy)phenyl | |
| 440) | formyl | H | 2,4-difluorophenyl | 4-(difluoromethoxy)phenyl | |
| 441) | formyl | H | 2,4-difluorophenyl | 3-(difluoromethoxy)phenyl | |
| 442) | formyl | H | 2,4-difluorophenyl | 4-cyanophenyl | |
| 443) | formyl | H | 4-trifluoromethylphenyl | phenyl | |
| 444) | formyl | H | 4-trifluoromethylphenyl | 4-ethylphenyl | |
| 445) | formyl | H | 4-trifluoromethylphenyl | 4-formylphenyl | |
| 446) | formyl | H | 4-trifluoromethylphenyl | 2-formylphenyl | |
| 447) | formyl | H | 4-trifluoromethylphenyl | 3-formylphenyl | |
| 448) | formyl | H | 4-trifluoromethylphenyl | 4-fluorophenyl | |
| 449) | formyl | H | 4-trifluoromethylphenyl | 2,4-difluorophenyl | |
| 450) | formyl | H | 4-trifluoromethylphenyl | 4-chlorophenyl | |
| 451) | formyl | H | 4-trifluoromethylphenyl | 3-chlorophenyl | |
| 452) | formyl | H | 4-trifluoromethylphenyl | 2-chlorophenyl | |
| 453) | formyl | H | 4-trifluoromethylphenyl | 4-chloro-2-methoxyphenyl | |
| 454) | formyl | H | 4-trifluoromethylphenyl | 4-trifluoromethylphenyl | |
| 455) | formyl | H | 4-trifluoromethylphenyl | 2-trifluoromethylphenyl | |
| 456) | formyl | H | 4-trifluoromethylphenyl | 3-trifluoromethylphenyl | |
| 457) | formyl | H | 4-trifluoromethylphenyl | 4-(trifluoromethoxy)phenyl | |
| 458) | formyl | H | 4-trifluoromethylphenyl | 3-(trifluoromethoxy)phenyl | |
| 459) | formyl | H | 4-trifluoromethylphenyl | 4-(difluoromethoxy)phenyl | |
| 460) | formyl | H | 4-trifluoromethylphenyl | 3-(difluoromethoxy)phenyl | |
| 461) | formyl | H | 4-trifluoromethylphenyl | 4-cyanophenyl | |
| 462) | formyl | H | 3,4-dichlorophenyl | 4-fluorophenyl | |
| 463) | formyl | H | 3,4-(formylenedioxy)phenyl | phenyl | |
| 464) | formyl | H | 3-trifluoromethylphenyl | phenyl | |
| 465) | formyl | H | 3-trifluoromethylphenyl | 4-ethylphenyl | |
| 466) | formyl | H | 3-trifluoromethylphenyl | 4-formylphenyl | |
| 467) | formyl | H | 3-trifluoromethylphenyl | 2-formylphenyl | |
| 468) | formyl | H | 3-trifluoromethylphenyl | 3-formylphenyl | |

TABLE 1-continued

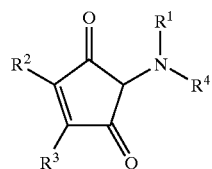

| No. | R¹ | R² | R³ | R⁴ | Phys. Data |
|---|---|---|---|---|---|
| 469) | formyl | H | 3-trifluoromethylphenyl | 4-fluorophenyl | |
| 470) | formyl | H | 3-trifluoromethylphenyl | 2,4-difluorophenyl | |
| 471) | formyl | H | 3-trifluoromethylphenyl | 4-chlorophenyl | |
| 472) | formyl | H | 3-trifluoromethylphenyl | 3-chlorophenyl | |
| 473) | formyl | H | 3-trifluoromethylphenyl | 2-chlorophenyl | |
| 474) | formyl | H | 3-trifluoromethylphenyl | 4-chloro-2-methoxyphenyl | |
| 475) | formyl | H | 3-trifluoromethylphenyl | 4-trifluoromethylphenyl | |
| 476) | formyl | H | 3-trifluoromethylphenyl | 2-trifluoromethylphenyl | |
| 477) | formyl | H | 3-trifluoromethylphenyl | 3-trifluoromethylphenyl | |
| 478) | formyl | H | 3-trifluoromethylphenyl | 4-(trifluoromethoxy)phenyl | |
| 479) | formyl | H | 3-trifluoromethylphenyl | 3-(trifluoromethoxy)phenyl | |
| 480) | formyl | H | 3-trifluoromethylphenyl | 4-(difluoromethoxy)phenyl | |
| 481) | formyl | H | 3-trifluoromethylphenyl | 3-(difluoromethoxy)phenyl | |
| 482) | formyl | H | 3-trifluoromethylphenyl | 4-cyanophenyl | |
| 483) | formyl | H | 4-formylphenyl | phenyl | |
| 484) | formyl | H | 4-methoxyphenyl | phenyl | |
| 485) | formyl | H | 4-chlorophenyl | phenyl | m.p. 145–146° C. |
| 486) | H | methyl | phenyl | phenyl | |
| 487) | H | methyl | phenyl | 4-methylphenyl | |
| 488) | H | methyl | phenyl | 2,4-dichlorophenyl | |
| 489) | H | methyl | 4-methylphenyl | phenyl | |
| 490) | H | methyl | 4-methylphenyl | 4-chlorophenyl | |
| 491) | H | methyl | 4-methoxyphenyl | phenyl | |
| 492) | H | methyl | 4-methoxyphenyl | 4-methoxyphenyl | |
| 493) | H | methyl | 4-methoxyphenyl | 2-methoxyphenyl | |
| 494) | H | methyl | 4-methoxyphenyl | 4-chlorophenyl | |
| 495) | H | methyl | 4-methoxyphenyl | 2,4-dichlorophenyl | |
| 496) | H | methyl | 3-chlorophenyl | phenyl | |
| 497) | H | methyl | 3,4-dichlorophenyl | phenyl | |
| 498) | H | methyl | 4-chlorophenyl | phenyl | |
| 499) | H | methyl | 4-chlorophenyl | 4-chlorophenyl | |
| 500) | H | methyl | 4-chlorophenyl | 3,4-dichlorophenyl | |
| 501) | H | methyl | 4-chlorophenyl | 2,4-dichlorophenyl | |
| 502) | H | methyl | 4-chlorophenyl | 4-fluorophenyl | |
| 503) | H | methyl | 4-chlorophenyl | 4-methylphenyl | |
| 504) | H | methyl | 4-bromophenyl | 4-methoxyphenyl | |
| 505) | H | methyl | 4-bromophenyl | 4-methylphenyl | |
| 506) | methyl | methyl | 4-methylphenyl | phenyl | |
| 507) | methyl | methyl | 4-methoxyphenyl | phenyl | |
| 508) | methyl | methyl | 4-chlorophenyl | phenyl | |

TABLE 1-continued

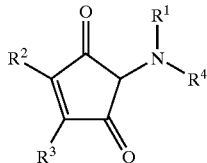

| No. | R¹ | R² | R³ | R⁴ | Phys. Data |
|---|---|---|---|---|---|
| 509) | H | methyl | phenyl | 4-isopropyl-phenyl | |
| 510) | H | methyl | phenyl | 4-fluorophenyl | |
| 511) | H | methyl | phenyl | 3-fluorophenyl | |
| 512) | H | methyl | phenyl | 2-fluorophenyl | |
| 513) | H | methyl | phenyl | 2,3,5,6-tetra-fluorophenyl | |
| 514) | H | methyl | phenyl | 4-trifluoro-methylphenyl | |
| 515) | H | methyl | phenyl | 3-trifluoro-methylphenyl | |
| 516) | H | methyl | phenyl | 4-methyl-sulfonylphenyl | |
| 517) | H | Methyl | phenyl | 4-chlorophenyl | |
| 518) | H | methyl | phenyl | 3-chlorophenyl | |
| 519) | H | methyl | phenyl | 2-chlorophenyl | |
| 520) | H | methyl | phenyl | 3,5-dichloro-phenyl | |
| 521) | H | methyl | phenyl | 4-(trifluoro-methoxy)phenyl | |
| 522) | H | methyl | phenyl | 3-(trifluoro-methoxy)phenyl | |
| 523) | H | methyl | phenyl | 4-(difluoro-methoxy)phenyl | |
| 524) | H | methyl | phenyl | 3-(difluoro-methoxy)phenyl | |
| 525) | H | methyl | phenyl | 4-cyanophenyl | |
| 526) | H | methyl | 4-chlorophenyl | 4-trifluoro-methylphenyl | |
| 527) | H | methyl | 4-chlorophenyl | 3-trifluoro-methylphenyl | |
| 528) | H | methyl | 4-chlorophenyl | 2-chlorophenyl | |
| 529) | H | methyl | 4-chlorophenyl | 3-chlorophenyl | |
| 530) | H | methyl | 4-chlorophenyl | 4-trifluoro-methoxyphenyl | |
| 531) | H | methyl | 4-chlorophenyl | 3-trifluoro-methoxyphenyl | |
| 532) | H | methyl | 4-chlorophenyl | 4-difluoro-methoxyphenyl | |
| 533) | H | methyl | 4-chlorophenyl | 3-difluoro-methoxyphenyl | |
| 534) | H | methyl | 4-fluorophenyl | phenyl | |
| 535) | H | methyl | 4-fluorophenyl | 4-ethylphenyl | |
| 536) | H | methyl | 4-fluorophenyl | 4-methylphenyl | |
| 537) | H | methyl | 4-fluorophenyl | 2-methylphenyl | |
| 538) | H | methyl | 4-fluorophenyl | 3-methylphenyl | |
| 539) | H | methyl | 4-fluorophenyl | 4-fluorophenyl | |
| 540) | H | methyl | 4-fluorophenyl | 2,4-difluoro-phenyl | |
| 541) | H | methyl | 4-fluorophenyl | 4-chlorophenyl | |
| 542) | H | methyl | 4-fluorophenyl | 3-chlorophenyl | |
| 543) | H | methyl | 4-fluorophenyl | 2-chlorophenyl | |
| 544) | H | methyl | 4-fluorophenyl | 4-chloro-2-methoxyphenyl | |
| 545) | H | methyl | 4-fluorophenyl | 4-trifluoro-methylphenyl | |
| 546) | H | methyl | 4-fluorophenyl | 2-trifluoro-methylphenyl | |
| 547) | H | methyl | 4-fluorophenyl | 3-trifluoro-methylphenyl | |
| 548) | H | methyl | 4-fluorophenyl | 4-(trifluoro-methoxy)phenyl | |
| 549) | H | methyl | 4-fluorophenyl | 3-(trifluoro-methoxy)phenyl | |
| 550) | H | methyl | 4-fluorophenyl | 4-(difluoro-methoxy)phenyl | |
| 551) | H | methyl | 4-fluorophenyl | 3-(difluoro-methoxy)phenyl | |
| 552) | H | methyl | 4-fluorophenyl | 4-cyanophenyl | |
| 553) | H | methyl | 3-fluorophenyl | phenyl | |
| 554) | H | methyl | 3-fluorophenyl | 4-ethylphenyl | |
| 555) | H | methyl | 3-fluorophenyl | 4-methylphenyl | |
| 556) | H | methyl | 3-fluorophenyl | 2-methylphenyl | |
| 557) | H | methyl | 3-fluorophenyl | 3-methylphenyl | |
| 558) | H | methyl | 3-fluorophenyl | 4-fluorophenyl | |
| 559) | H | methyl | 3-fluorophenyl | 2,4-difluoro-phenyl | |
| 560) | H | methyl | 3-fluorophenyl | 4-chlorophenyl | |
| 561) | H | methyl | 3-fluorophenyl | 3-chlorophenyl | |
| 562) | H | methyl | 3-fluorophenyl | 2-chlorophenyl | |
| 563) | H | methyl | 3-fluorophenyl | 4-chloro-2-methoxyphenyl | |
| 564) | H | methyl | 3-fluorophenyl | 4-trifluoro-methylphenyl | |
| 565) | H | methyl | 3-fluorophenyl | 2-trifluoro-methylphenyl | |
| 566) | H | methyl | 3-fluorophenyl | 3-trifluoro-methylphenyl | |
| 567) | H | methyl | 3-fluorophenyl | 4-(trifluoro-methoxy)phenyl | |
| 568) | H | methyl | 3-fluorophenyl | 3-(trifluoro-methoxy)phenyl | |
| 569) | H | methyl | 3-fluorophenyl | 4-(difluoro-methoxy)phenyl | |
| 570) | H | methyl | 3-fluorophenyl | 3-(difluoro-methoxy)phenyl | |
| 571) | H | methyl | 3-fluorophenyl | 4-cyanophenyl | |
| 572) | H | methyl | 2-fluorophenyl | phenyl | |
| 573) | H | methyl | 2-fluorophenyl | 4-ethylphenyl | |
| 574) | H | methyl | 2-fluorophenyl | 4-methylphenyl | |
| 575) | H | methyl | 2-fluorophenyl | 2-methylphenyl | |
| 576) | H | methyl | 2-fluorophenyl | 3-methylphenyl | |
| 577) | H | methyl | 2-fluorophenyl | 4-fluorophenyl | |
| 578) | H | methyl | 2-fluorophenyl | 2,4-difluoro-phenyl | |
| 579) | H | methyl | 2-fluorophenyl | 4-chlorophenyl | |
| 580) | H | methyl | 2-fluorophenyl | 3-chlorophenyl | |
| 581) | H | methyl | 2-fluorophenyl | 2-chlorophenyl | |
| 582) | H | methyl | 2-fluorophenyl | 4-chloro-2-methoxyphenyl | |
| 583) | H | methyl | 2-fluorophenyl | 4-trifluoro-methylphenyl | |
| 584) | H | methyl | 2-fluorophenyl | 2-trifluoro-methylphenyl | |
| 585) | H | methyl | 2-fluorophenyl | 3-trifluoro-methylphenyl | |
| 586) | H | methyl | 2-fluorophenyl | 4-(trifluoro-methoxy)phenyl | |
| 587) | H | methyl | 2-fluorophenyl | 3-(trifluoro-methoxy)phenyl | |
| 588) | H | methyl | 2-fluorophenyl | 4-(difluoro-methoxy)phenyl | |
| 589) | H | methyl | 2-fluorophenyl | 3-(difluoro-methoxy)phenyl | |
| 590) | H | methyl | 2-fluorophenyl | 4-cyanophenyl | |
| 591) | H | methyl | 2,4-difluoro-phenyl | phenyl | |
| 592) | H | methyl | 2,4-difluoro-phenyl | 4-ethylphenyl | |
| 593) | H | methyl | 2,4-difluoro-phenyl | 4-methylphenyl | |
| 594) | H | methyl | 2,4-difluoro-phenyl | 2-methylphenyl | |

TABLE 1-continued

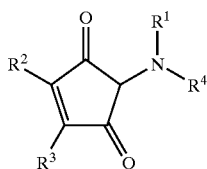

| No. | R¹ | R² | R³ | R⁴ | Phys. Data |
|---|---|---|---|---|---|
| 595) | H | methyl | 2,4-difluorophenyl | 3-methylphenyl | |
| 596) | H | methyl | 2,4-difluorophenyl | 4-fluorophenyl | |
| 597) | H | methyl | 2,4-difluorophenyl | 2,4-difluorophenyl | |
| 598) | H | methyl | 2,4-difluorophenyl | 4-chlorophenyl | |
| 599) | H | methyl | 2,4-difluorophenyl | 3-chlorophenyl | |
| 600) | H | methyl | 2,4-difluorphenyl | 2-chlorophenyl | |
| 601) | H | methyl | 2,4-difluorophenyl | 4-chloro-2-methoxyphenyl | |
| 602) | H | methyl | 2,4-difluorophenyl | 4-trifluoromethylphenyl | |
| 603) | H | methyl | 2,4-difluorophenyl | 2-trifluoromethylphenyl | |
| 604) | H | methyl | 2,4-difluorophenyl | 3-trifluoromethylphenyl | |
| 605) | H | methyl | 2,4-difluorophenyl | 4-(trifluoromethoxy)phenyl | |
| 606) | H | methyl | 2,4-difluorophenyl | 3-(trifluoromethoxy)phenyl | |
| 607) | H | methyl | 2,4-difluorophenyl | 4-(difluoromethoxy)phenyl | |
| 608) | H | methyl | 2,4-difluorophenyl | 3-(difluoromethoxy)phenyl | |
| 609) | H | methyl | 2,4-difluorophenyl | 4-cyanophenyl | |
| 610) | H | methyl | 4-trifluoromethylphenyl | phenyl | |
| 611) | H | methyl | 4-trifluoromethylphenyl | 4-ethylphenyl | |
| 612) | H | methyl | 4-trifluoromethylphenyl | 4-methylphenyl | |
| 613) | H | methyl | 4-trifluoromethylphenyl | 2-methylphenyl | |
| 614) | H | methyl | 4-trifluoromethylphenyl | 3-methylphenyl | |
| 615) | H | methyl | 4-trifluoromethylphenyl | 4-fluorophenyl | |
| 616) | H | methyl | 4-trifluoromethylphenyl | 2,4-difluorophenyl | |
| 617) | H | methyl | 4-trifluoromethylphenyl | 4-chlorophenyl | |
| 618) | H | methyl | 4-trifluoromethylphenyl | 3-chlorophenyl | |
| 619) | H | methyl | 4-trifluoromethylphenyl | 2-chlorophenyl | |
| 620) | H | methyl | 4-trifluoromethylphenyl | 4-chloro-2-methoxyphenyl | |
| 621) | H | methyl | 4-trifluoromethylphenyl | 4-trifluoromethylphenyl | |
| 622) | H | methyl | 4-trifluoromethylphenyl | 2-trifluoromethylphenyl | |
| 623) | H | methyl | 4-trifluoromethylphenyl | 3-trifluoromethylphenyl | |
| 624) | H | methyl | 4-trifluoromethylphenyl | 4-(trifluoromethoxy)phenyl | |
| 625) | H | methyl | 4-trifluoromethylphenyl | 3-(trifluoromethoxy)phenyl | |
| 626) | H | methyl | 4-trifluoromethylphenyl | 4-(difluoromethoxy)phenyl | |
| 627) | H | methyl | 4-trifluoromethylphenyl | 3-(difluoromethoxy)phenyl | |

TABLE 1-continued

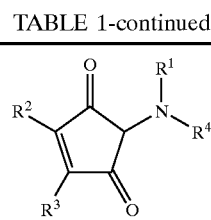

| No. | R¹ | R² | R³ | R⁴ | Phys. Data |
|---|---|---|---|---|---|
| 628) | H | methyl | 4-trifluoromethylphenyl | 4-cyanophenyl | |
| 629) | H | methyl | 3,4-dichlorophenyl | 4-fluorophenyl | |
| 630) | H | methyl | 3,4-(methylenedioxy)phenyl | phenyl | |
| 631) | H | methyl | 3-trifluoromethylphenyl | phenyl | |
| 632) | H | methyl | 3-trifluoromethylphenyl | 4-ethylphenyl | |
| 633) | H | methyl | 3-trifluoromethylphenyl | 4-methylphenyl | |
| 634) | H | methyl | 3-trifluoromethylphenyl | 2-methylphenyl | |
| 635) | H | methyl | 3-trifluoromethylphenyl | 3-methylphenyl | |
| 636) | H | methyl | 3-trifluoromethylphenyl | 4-fluorophenyl | |
| 637) | H | methyl | 3-trifluoromethylphenyl | 2,4-difluorophenyl | |
| 638) | H | methyl | 3-trifluoromethylphenyl | 4-chlorophenyl | |
| 639) | H | methyl | 3-trifluoromethylphenyl | 3-chlorophenyl | |
| 640) | H | methyl | 3-trifluoromethylphenyl | 2-chlorophenyl | |
| 641) | H | methyl | 3-trifluoromethylphenyl | 4-chloro-2-methylphenyl | |
| 642) | H | methyl | 3-trifluoromethylphenyl | 4-trifluoromethylphenyl | |
| 643) | H | methyl | 3-trifluoromethylphenyl | 2-trifluoromethylphenyl | |
| 644) | H | methyl | 3-trifluoromethylphenyl | 3-trifluoromethylphenyl | |
| 645) | H | methyl | 3-trifluoromethylphenyl | 4-(trifluoromethoxy)phenyl | |
| 646) | H | methyl | 3-trifluoromethylphenyl | 3-(trifluoromethoxy)phenyl | |
| 647) | H | methyl | 3-trifluoromethylphenyl | 4-(difluoromethoxy)phenyl | |
| 648) | H | methyl | 3-trifluoromethylphenyl | 3-(difluoromethoxy)phenyl | |
| 649) | H | methyl | 3-trifluoromethylphenyl | 4-cyanophenyl | |
| 650) | methyl | methyl | phenyl | phenyl | |
| 651) | methyl | methyl | phenyl | 4-methylphenyl | |
| 652) | methyl | methyl | phenyl | 2,4-dichlorophenyl | |
| 653) | methyl | methyl | 4-methylphenyl | 4-chlorophenyl | |
| 654) | methyl | methyl | 4-methoxyphenyl | 4-methoxyphenyl | |
| 655) | methyl | methyl | 4-methoxyphenyl | 2-methoxyphenyl | |
| 656) | methyl | methyl | 4-methoxyphenyl | 4-chlorophenyl | |
| 657) | methyl | methyl | 4-methoxyphenyl | 2,4-dichlorophenyl | |
| 658) | methyl | methyl | 3-chlorophenyl | phenyl | |
| 659) | methyl | methyl | 3,4-dichlorophenyl | phenyl | |
| 660) | methyl | methyl | 4-chlorophenyl | 4-chlorophenyl | |
| 661) | methyl | methyl | 4-chlorophenyl | 3,4-dichlorophenyl | |
| 662) | Methyl | methyl | 4-chlorophenyl | 2,4-dichlorophenyl | |
| 663) | methyl | methyl | 4-chlorophenyl | 4-fluorophenyl | |
| 664) | methyl | methyl | 4-chlorophenyl | 4-methylphenyl | |
| 665) | methyl | methyl | 4-bromophenyl | 4-methoxyphenyl | |

TABLE 1-continued

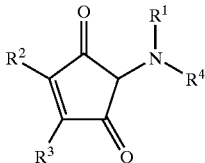

| No. | R¹ | R² | R³ | R⁴ | Phys. Data |
|---|---|---|---|---|---|
| 666) | methyl | methyl | 4-bromophenyl | 4-methylphenyl | |
| 667) | methyl | methyl | phenyl | 4-isopropylphenyl | |
| 668) | methyl | methyl | phenyl | 4-fluorophenyl | |
| 669) | methyl | methyl | phenyl | 3-fluorophenyl | |
| 670) | methyl | methyl | phenyl | 2-fluorophenyl | |
| 671) | methyl | methyl | phenyl | 2,3,5,6-tetrafluorophenyl | |
| 672) | methyl | methyl | phenyl | 4-trifluoromethylphenyl | |
| 673) | methyl | methyl | phenyl | 3-trifluoromethylphenyl | |
| 674) | methyl | methyl | phenyl | 4-methylsulphonylphenyl | |
| 675) | methyl | methyl | phenyl | 4-chlorophenyl | |
| 676) | methyl | methyl | phenyl | 3-chlorophenyl | |
| 677) | methyl | methyl | phenyl | 2-chlorophenyl | |
| 678) | methyl | methyl | phenyl | 3,5-dichlorophenyl | |
| 679) | methyl | methyl | phenyl | 4-(trifluoromethoxy)phenyl | |
| 680) | methyl | methyl | phenyl | 3-(trifluoromethoxy)phenyl | |
| 681) | methyl | methyl | phenyl | 4-(difluoromethoxy)phenyl | |
| 682) | methyl | methyl | phenyl | 3-(difluoromethoxy)phenyl | |
| 683) | methyl | methyl | phenyl | 4-cyanophenyl | |
| 684) | methyl | methyl | 4-chlorophenyl | 4-trifluoromethylphenyl | |
| 685) | methyl | methyl | 4-chlorophenyl | 3-trifluoromethylphenyl | |
| 686) | methyl | methyl | 4-chlorophenyl | 2-chlorophenyl | |
| 687) | methyl | methyl | 4-chlorophenyl | 3-chlorophenyl | |
| 688) | methyl | methyl | 4-chlorophenyl | 4-trifluoromethoxyphenyl | |
| 689) | methyl | methyl | 4-chlorophenyl | 3-trifluoromethoxyphenyl | |
| 690) | methyl | methyl | 4-chlorophenyl | 4-difluoromethoxyphenyl | |
| 691) | methyl | methyl | 4-chlorophenyl | 3-difluoromethoxyphenyl | |
| 692) | methyl | methyl | 4-fluorophenyl | phenyl | |
| 693) | methyl | methyl | 4-fluorophenyl | 4-ethylphenyl | |
| 694) | methyl | methyl | 4-fluorophenyl | 4-methylphenyl | |
| 695) | methyl | methyl | 4-fluorophenyl | 2-methylphenyl | |
| 696) | methyl | methyl | 4-fluorophenyl | 3-methylphenyl | |
| 697) | methyl | methyl | 4-fluorophenyl | 4-fluorophenyl | |
| 698) | methyl | methyl | 4-fluorophenyl | 2,4-difluorophenyl | |
| 699) | methyl | methyl | 4-fluorophenyl | 4-chlorophenyl | |
| 700) | methyl | methyl | 4-fluorophenyl | 3-chlorophenyl | |
| 701) | methyl | methyl | 4-fluorophenyl | 2-chlorophenyl | |
| 702) | methyl | methyl | 4-fluorophenyl | 4-chloro-2-methoxyphenyl | |
| 703) | methyl | methyl | 4-fluorophenyl | 4-trifluoromethylphenyl | |
| 704) | methyl | methyl | 4-fluorophenyl | 2-trifluoromethylphenyl | |
| 705) | methyl | methyl | 4-fluorophenyl | 3-trifluoromethylphenyl | |
| 706) | methyl | methyl | 4-fluorophenyl | 4-(trifluoromethoxy)phenyl | |
| 707) | methyl | methyl | 4-fluorophenyl | 3-(trifluoromethoxy)phenyl | |
| 708) | methyl | methyl | 4-fluorophenyl | 4-(difluoromethoxy)phenyl | |
| 709) | methyl | methyl | 4-fluorophenyl | 3-(difluoromethoxy)phenyl | |
| 710) | methyl | methyl | 4-fluorophenyl | 4-cyanophenyl | |
| 711) | methyl | methyl | 3-fluorophenyl | phenyl | |
| 712) | methyl | methyl | 3-fluorophenyl | 4-ethylphenyl | |
| 713) | methyl | methyl | 3-fluorophenyl | 4-methylphenyl | |
| 714) | methyl | methyl | 3-fluorophenyl | 2-methylphenyl | |
| 715) | methyl | methyl | 3-fluorophenyl | 3-methylphenyl | |
| 716) | methyl | methyl | 3-fluorophenyl | 4-fluorophenyl | |
| 717) | methyl | methyl | 3-fluorophenyl | 2,4-difluorophenyl | |
| 718) | methyl | methyl | 3-fluorophenyl | 4-chlorophenyl | |
| 719) | methyl | methyl | 3-fluorophenyl | 3-chlorophenyl | |
| 720) | methyl | methyl | 3-fluorophenyl | 2-chlorophenyl | |
| 721) | methyl | methyl | 3-fluorophenyl | 4-chloro-2-methoxyphenyl | |
| 722) | methyl | methyl | 3-fluorophenyl | 4-trifluoromethylphenyl | |
| 723) | methyl | methyl | 3-fluorophenyl | 2-trifluoromethylphenyl | |
| 724) | methyl | methyl | 3-fluorophenyl | 3-trifluoromethylphenyl | |
| 725) | methyl | methyl | 3-fluorophenyl | 4-(trifluoromethoxy)phenyl | |
| 726) | methyl | methyl | 3-fluorophenyl | 3-(trifluoromethoxy)phenyl | |
| 727) | methyl | methyl | 3-fluorophenyl | 4-(difluoromethoxy)phenyl | |
| 728) | methyl | methyl | 3-fluorophenyl | 3-(difluoromethoxy)phenyl | |
| 729) | methyl | methyl | 3-fluorophenyl | 4-cyanophenyl | |
| 730) | methyl | methyl | 2-fluorophenyl | phenyl | |
| 731) | methyl | methyl | 2-fluorophenyl | 4-ethylphenyl | |
| 732) | methyl | methyl | 2-fluorophenyl | 4-methylphenyl | |
| 733) | methyl | methyl | 2-fluorophenyl | 2-methylphenyl | |
| 734) | methyl | methyl | 2-fluorophenyl | 3-methylphenyl | |
| 735) | methyl | methyl | 2-fluorophenyl | 4-fluorophenyl | |
| 736) | methyl | methyl | 2-fluorophenyl | 2,4-difluorophenyl | |
| 737) | methyl | methyl | 2-fluorophenyl | 4-chlorophenyl | |
| 738) | methyl | methyl | 2-fluorophenyl | 3-chlorophenyl | |
| 739) | methyl | methyl | 2-fluorophenyl | 2-chlorophenyl | |
| 740) | methyl | methyl | 2-fluorophenyl | 4-chloro-2-methoxyphenyl | |
| 741) | methyl | methyl | 2-fluorophenyl | 4-trifluoromethylphenyl | |
| 742) | methyl | methyl | 2-fluorophenyl | 2-trifluoromethylphenyl | |
| 743) | methyl | methyl | 2-fluorophenyl | 3-trifluoromethylphenyl | |
| 744) | methyl | methyl | 2-fluorophenyl | 4-(trifluoromethoxy)phenyl | |
| 745) | methyl | methyl | 2-fluorophenyl | 3-(trifluoromethoxy)phenyl | |
| 746) | methyl | methyl | 2-fluorophenyl | 4-(difluoromethoxy)phenyl | |
| 747) | methyl | methyl | 2-fluorophenyl | 3-(difluoromethoxy)phenyl | |
| 748) | methyl | methyl | 2-fluorophenyl | 4-cyanophenyl | |
| 749) | methyl | methyl | 2,4-difluorophenyl | phenyl | |
| 750) | methyl | methyl | 2,4-difluorophenyl | 4-ethylphenyl | |
| 751) | methyl | methyl | 2,4-difluorophenyl | 4-methylphenyl | |
| 752) | methyl | methyl | 2,4-difluorophenyl | 2-methylphenyl | |

TABLE 1-continued

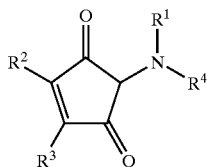

| No. | R¹ | R² | R³ | R⁴ | Phys. Data |
|---|---|---|---|---|---|
| 753) | methyl | methyl | 2,4-difluorophenyl | 3-methylphenyl | |
| 754) | methyl | methyl | 2,4-difluorophenyl | 4-fluorophenyl | |
| 755) | methyl | methyl | 2,4-difluorophenyl | 2,4-difluorophenyl | |
| 756) | methyl | methyl | 2,4-difluorophenyl | 4-chlorophenyl | |
| 757) | methyl | methyl | 2,4-difluorophenyl | 3-chlorophenyl | |
| 758) | methyl | methyl | 2,4-difluorophenyl | 2-chlorophenyl | |
| 759) | methyl | methyl | 2,4-difluorophenyl | 4-chloro-2-methoxyphenyl | |
| 760) | methyl | methyl | 2,4-difluorophenyl | 4-trifluoromethylphenyl | |
| 761) | methyl | methyl | 2,4-difluorophenyl | 2-trifluoromethylphenyl | |
| 762) | methyl | methyl | 2,4-difluorophenyl | 3-trifluoromethylphenyl | |
| 763) | methyl | methyl | 2,4-difluorophenyl | 4-(trifluoromethoxy)phenyl | |
| 764) | methyl | methyl | 2,4-difluorophenyl | 3-(trifluoromethoxy)phenyl | |
| 765) | methyl | methyl | 2,4-difluorophenyl | 4-(difluoromethoxy)phenyl | |
| 766) | methyl | methyl | 2,4-difluorophenyl | 3-(difluoromethoxy)phenyl | |
| 767) | methyl | methyl | 2,4-difluorophenyl | 4-cyanophenyl | |
| 768) | methyl | methyl | 4-trifluoromethylphenyl | phenyl | |
| 769) | methyl | methyl | 4-trifluoromethylphenyl | 4-ethylphenyl | |
| 770) | methyl | methyl | 4-trifluoromethylphenyl | 4-methylphenyl | |
| 771) | methyl | methyl | 4-trifluoromethylphenyl | 2-methylphenyl | |
| 772) | methyl | methyl | 4-trifluoromethylphenyl | 3-methylphenyl | |
| 773) | methyl | methyl | 4-trifluoromethylphenyl | 4-fluorophenyl | |
| 774) | methyl | methyl | 4-trifluoromethylphenyl | 2,4-difluorophenyl | |
| 775) | methyl | methyl | 4-trifluoromethylphenyl | 4-chlorophenyl | |
| 776) | methyl | methyl | 4-trifluoromethylphenyl | 3-chlorophenyl | |
| 777) | methyl | methyl | 4-trifluoromethylphenyl | 2-chlorophenyl | |
| 778) | methyl | methyl | 4-trifluoromethylphenyl | 4-chloro-2-methoxyphenyl | |
| 779) | methyl | methyl | 4-trifluoromethylphenyl | 4-trifluoromethylphenyl | |
| 780) | methyl | methyl | 4-trifluoromethylphenyl | 2-trifluoromethylphenyl | |
| 781) | methyl | methyl | 4-trifluoromethylphenyl | 3-trifluoromethylphenyl | |
| 782) | methyl | methyl | 4-trifluoromethylphenyl | 4-(trifluoromethoxy)phenyl | |
| 783) | methyl | methyl | 4-trifluoromethylphenyl | 3-(trifluoromethoxy)phenyl | |
| 784) | methyl | methyl | 4-trifluoromethylphenyl | 4-(difluoromethoxy)phenyl | |
| 785) | methyl | methyl | 4-trifluoromethylphenyl | 3-(difluoromethoxy)phenyl | |
| 786) | methyl | methyl | 4-trifluoromethylphenyl | 4-cyanophenyl | |
| 787) | methyl | methyl | 3,4-dichlorophenyl | 4-fluorophenyl | |
| 788) | methyl | methyl | 3,4-(methylenedioxy)phenyl | phenyl | |
| 789) | methyl | methyl | 3-trifluoromethylphenyl | phenyl | |
| 790) | methyl | methyl | 3-trifluoromethylphenyl | 4-ethylphenyl | |
| 791) | methyl | methyl | 3-trifluoromethylphenyl | 4-methylphenyl | |
| 792) | methyl | methyl | 3-trifluoromethylphenyl | 2-methylphenyl | |
| 793) | methyl | methyl | 3-trifluoromethylphenyl | 3-methylphenyl | |
| 794) | methyl | methyl | 3-trifluoromethylphenyl | 4-fluorophenyl | |
| 795) | methyl | methyl | 3-trifluoromethylphenyl | 2,4-difluorophenyl | |
| 796) | methyl | methyl | 3-trifluoromethylphenyl | 4-chlorophenyl | |
| 797) | methyl | methyl | 3-trifluoromethylphenyl | 3-chlorophenyl | |
| 798) | methyl | methyl | 3-trifluoromethylphenyl | 2-chlorophenyl | |
| 799) | methyl | methyl | 3-trifluoromethylphenyl | 4-chloro-2-methoxyphenyl | |
| 800) | methyl | methyl | 3-trifluoromethylphenyl | 4-trifluoromethylphenyl | |
| 801) | methyl | methyl | 3-trifluoromethylphenyl | 2-trifluoromethylphenyl | |
| 802) | methyl | methyl | 3-trifluoromethylphenyl | 3-trifluoromethylphenyl | |
| 803) | methyl | methyl | 3-trifluoromethylphenyl | 4-(trifluoromethoxy)phenyl | |
| 804) | methyl | methyl | 3-trifluoromethylphenyl | 3-(trifluoromethoxy)phenyl | |
| 805) | methyl | methyl | 3-trifluoromethylphenyl | 4-(difluoromethoxy)phenyl | |
| 806) | methyl | methyl | 3-trifluoromethylphenyl | 3-(difluoromethoxy)phenyl | |
| 807) | methyl | methyl | 3-trifluoromethylphenyl | 4-cyanophenyl | |
| 808) | formyl | methyl | phenyl | phenyl | |
| 809) | formyl | methyl | phenyl | 4-methylphenyl | |
| 810) | formyl | methyl | phenyl | 2,4-dichlorophenyl | |
| 811) | formyl | methyl | 4-methylphenyl | 4-chlorophenyl | |
| 812) | formyl | methyl | 4-methoxyphenyl | 4-methoxyphenyl | |
| 813) | formyl | methyl | 4-methoxyphenyl | 2-methoxyphenyl | |
| 814) | formyl | methyl | 4-methoxyphenyl | 4-chlorophenyl | |
| 815) | formyl | methyl | 4-methoxyphenyl | 2,4-dichlorophenyl | |
| 816) | formyl | methyl | 3-chlorophenyl | phenyl | |
| 817) | formyl | methyl | 3,4-dichlorophenyl | phenyl | |
| 818) | formyl | methyl | 4-chlorophenyl | 4-chlorophenyl | |
| 819) | formyl | methyl | 4-chlorophenyl | 3,4-dichlorophenyl | |
| 820) | formyl | methyl | 4-chlorophenyl | 2,4-dichlorophenyl | |
| 821) | formyl | methyl | 4-chlorophenyl | 4-fluorophenyl | |

TABLE 1-continued

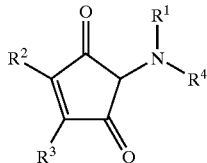

| No. | $R^1$ | $R^2$ | $R^3$ | $R^4$ | Phys. Data |
|---|---|---|---|---|---|
| 822) | formyl | methyl | 4-chlorophenyl | 4-formylphenyl | |
| 823) | formyl | methyl | 4-bromophenyl | 4-methoxyphenyl | |
| 824) | formyl | methyl | 4-bromophenyl | 4-methoxyphenyl | |
| 825) | formyl | methyl | phenyl | 4-isopropylphenyl | |
| 826) | forxnyl | methyl | phenyl | 4-fluorophenyl | |
| 827) | formyl | methyl | phenyl | 3-fluorophenyl | |
| 828) | formyl | methyl | phenyl | 2-fluorophenyl | |
| 829) | formyl | methyl | phenyl | 2,3,5,6-tetrafluorophenyl | |
| 830) | formyl | methyl | phenyl | 4-trifluoromethylphenyl | |
| 831) | formyl | methyl | phenyl | 3-trifluoromethylphenyl | |
| 832) | formyl | methyl | phenyl | 4-formylsulfonylphenyl | |
| 833) | formyl | methyl | phenyl | 4-chlorophenyl | |
| 834) | formyl | methyl | phenyl | 3-chlorophenyl | |
| 835) | formyl | methyl | phenyl | 2-chlorophenyl | |
| 836) | formyl | methyl | phenyl | 3,5-dichlorophenyl | |
| 837) | formyl | methyl | phenyl | 4-(trifluoromethoxy)phenyl | |
| 838) | formyl | methyl | phenyl | 3-(trifluoromethoxy)phenyl | |
| 839) | formyl | methyl | phenyl | 4-(difluoromethoxy)phenyl | |
| 840) | formyl | methyl | phenyl | 3-(difluoromethoxy)phenyl | |
| 841) | formyl | methyl | phenyl | 4-cyanophenyl | |
| 842) | formyl | methyl | 4-chlorophenyl | 4-trifluoromethylphenyl | |
| 843) | formyl | methyl | 4-chlorophenyl | 3-trifluoromethylphenyl | |
| 844) | formyl | methyl | 4-chlorophenyl | 2-chlorophenyl | |
| 845) | formyl | methyl | 4-chlorophenyl | 3-chlorophenyl | |
| 846) | formyl | methyl | 4-chlorophenyl | 4-trifluoromethoxyphenyl | |
| 847) | formyl | methyl | 4-chlorophenyl | 3-trifluoromethoxyphenyl | |
| 848) | formyl | methyl | 4-chlorophenyl | 4-difluoromethoxyphenyl | |
| 849) | formyl | methyl | 4-chlorophenyl | 3-difluoromethoxyphenyl | |
| 850) | formyl | methyl | 4-fluorophenyl | phenyl | |
| 851) | formyl | methyl | 4-fluorophenyl | 4-ethylphenyl | |
| 852) | formyl | methyl | 4-fluorophenyl | 4-formylphenyl | |
| 853) | formyl | methyl | 4-fluorophenyl | 2-formylphenyl | |
| 854) | formyl | methyl | 4-fluorophenyl | 3-formylphenyl | |
| 855) | formyl | methyl | 4-fluorophenyl | 4-fluorophenyl | |
| 856) | formyl | methyl | 4-fluorophenyl | 2,4-difluorophenyl | |
| 857) | formyl | methyl | 4-fluorophenyl | 4-chlorophenyl | |
| 858) | formyl | methyl | 4-fluorophenyl | 3-chlorophenyl | |
| 859) | formyl | methyl | 4-fluorophenyl | 2-chlorophenyl | |
| 860) | formyl | methyl | 4-fluorophenyl | 4-chloro-2-methoxyphenyl | |
| 861) | formyl | methyl | 4-fluorophenyl | 4-trifluoromethylphenyl | |
| 862) | formyl | methyl | 4-fluorophenyl | 2-trifluoromethylphenyl | |
| 863) | formyl | methyl | 4-fluorophenyl | 3-trifluoromethylphenyl | |
| 864) | formyl | methyl | 4-fluorophenyl | 4-(trifluoromethoxy)phenyl | |
| 865) | formyl | methyl | 4-fluorophenyl | 3-(trifluoromethoxy)phenyl | |

TABLE 1-continued

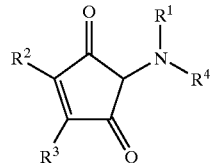

| No. | $R^1$ | $R^2$ | $R^3$ | $R^4$ | Phys. Data |
|---|---|---|---|---|---|
| 866) | formyl | methyl | 4-fluorophenyl | 4-(difluoromethoxy)phenyl | |
| 867) | formyl | methyl | 4-fluorophenyl | 3-(difluoromethoxy)phenyl | |
| 868) | formyl | methyl | 4-fluorophenyl | 4-cyanophenyl | |
| 869) | formyl | methyl | 3-fluorophenyl | phenyl | |
| 870) | formyl | methyl | 3-fluorophenyl | 4-ethylphenyl | |
| 871) | formyl | methyl | 3-fluorophenyl | 4-formylphenyl | |
| 872) | formyl | methyl | 3-fluorophenyl | 2-formylphenyl | |
| 873) | formyl | methyl | 3-fluorophenyl | 3-formylphenyl | |
| 874) | formyl | methyl | 3-fluorophenyl | 4-fluorophenyl | |
| 875) | formyl | methyl | 3-fluorophenyl | 2,4-difluorophenyl | |
| 876) | formyl | methyl | 3-fluorophenyl | 4-chlorophenyl | |
| 877) | formyl | methyl | 3-fluorophenyl | 3-chlorophenyl | |
| 878) | formyl | methyl | 3-fluorophenyl | 2-chlorophenyl | |
| 879) | formyl | methyl | 3-fluorophenyl | 4-chloro-2-methoxyphenyl | |
| 880) | formyl | methyl | 3-fluorophenyl | 4-trifluoromethylphenyl | |
| 881) | formyl | methyl | 3-fluorophenyl | 2-trifluoromethylphenyl | |
| 882) | formyl | methyl | 3-fluorophenyl | 3-trifluoromethylphenyl | |
| 883) | formyl | methyl | 3-fluorophenyl | 4-(trifluoromethoxy)phenyl | |
| 884) | formyl | methyl | 3-fluorophenyl | 3-(trifluoromethoxy)phenyl | |
| 885) | formyl | methyl | 3-fluorophenyl | 4-(difluoromethoxy)phenyl | |
| 886) | formyl | methyl | 3-fluorophenyl | 3-(difluoromethoxy)phenyl | |
| 887) | formyl | methyl | 3-fluorophenyl | 4-cyanophenyl | |
| 888) | formyl | methyl | 2-fluorophenyl | phenyl | |
| 889) | formyl | methyl | 2-fluorophenyl | 4-ethylphenyl | |
| 890) | formyl | methyl | 2-fluorophenyl | 4-formylphenyl | |
| 891) | formyl | methyl | 2-fluorophenyl | 2-formylphenyl | |
| 892) | formyl | methyl | 2-fluorophenyl | 3-formylphenyl | |
| 893) | formyl | methyl | 2-fluorophenyl | 4-Fluorphenyl | |
| 894) | Formyl | Methyl | 2-fluorophenyl | 2,4-difluorophenyl | |
| 895) | formyl | methyl | 2-fluorophenyl | 4-chlorophenyl | |
| 896) | formyl | methyl | 2-fluorophenyl | 3-chlorophenyl | |
| 897) | formyl | methyl | 2-fluorophenyl | 2-chlorophenyl | |
| 898) | formyl | methyl | 2-fluorophenyl | 4-chloro-2-methoxyphenyl | |
| 899) | formyl | methyl | 2-fluorophenyl | 4-trifluoromethylphenyl | |
| 900) | formyl | methyl | 2-fluorophenyl | 2-trifluoromethylphenyl | |
| 901) | formyl | methyl | 2-fluorophenyl | 3-trifluoromethylphenyl | |
| 902) | formyl | methyl | 2-fluorophenyl | 4-(trifluoromethoxy)phenyl | |
| 903) | formyl | methyl | 2-fluorophenyl | 3-(trifluoromethoxy)phenyl | |
| 904) | formyl | methyl | 2-fluorophenyl | 4-(difluoromethoxy)phenyl | |
| 905) | formyl | methyl | 2-fluorophenyl | 3-(difluoromethoxy)phenyl | |
| 906) | formyl | methyl | 2-fluorophenyl | 4-cyanophenyl | |
| 907) | formyl | methyl | 2,4-difluorophenyl | phenyl | |
| 908) | formyl | methyl | 2,4-difluorophenyl | 4-ethylphenyl | |
| 909) | formyl | methyl | 2,4-difluorophenyl | 4-formylphenyl | |

TABLE 1-continued

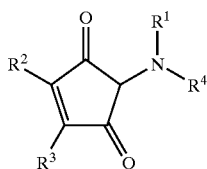

| No. | R¹ | R² | R³ | R⁴ | Phys. Data |
|---|---|---|---|---|---|
| 910) | formyl | methyl | 2,4-difluorophenyl | 2-formylphenyl | |
| 911) | formyl | methyl | 2,4-difluorophenyl | 3-formylphenyl | |
| 912) | formyl | methyl | 2,4-difluorophenyl | 4-fluorophenyl | |
| 913) | formyl | methyl | 2,4-difluorophenyl | 2,4-difluorophenyl | |
| 914) | formyl | methyl | 2,4-difluorophenyl | 4-chlorophenyl | |
| 915) | formyl | methyl | 2,4-difluorophenyl | 3-chlorophenyl | |
| 916) | formyl | methyl | 2,4-difluorophenyl | 2-chlorophenyl | |
| 917) | formyl | methyl | 2,4-difluorophenyl | 4-chloro-2-methoxyphenyl | |
| 918) | formyl | methyl | 2,4-difluorophenyl | 4-trifluoromethylphenyl | |
| 919) | formyl | methyl | 2,4-difluorophenyl | 2-trifluoromethylphenyl | |
| 920) | formyl | methyl | 2,4-difluorophenyl | 3-trifluoromethylphenyl | |
| 921) | formyl | methyl | 2,4-difluorophenyl | 4-(trifluoromethoxy)phenyl | |
| 922) | formyl | methyl | 2,4-difluorophenyl | 3-(trifluoromethoxy)phenyl | |
| 923) | formyl | methyl | 2,4-difluorophenyl | 4-(difluoromethoxy)phenyl | |
| 924) | formyl | methyl | 2,4-difluorophenyl | 3-(difluoromethoxy)phenyl | |
| 925) | formyl | methyl | 2,4-difluorophenyl | 4-cyanophenyl | |
| 926) | formyl | methyl | 4-trifluoromethylphenyl | phenyl | |
| 927) | formyl | methyl | 4-trifluoromethylphenyl | 4-ethylphenyl | |
| 928) | formyl | methyl | 4-trifluoromethylphenyl | 4-formylphenyl | |
| 929) | formyl | methyl | 4-trifluoromethylphenyl | 2-formylphenyl | |
| 930) | formyl | methyl | 4-trifluoromethylphenyl | 3-formylphenyl | |
| 931) | formyl | methyl | 4-trifluoromethylphenyl | 4-fluorophenyl | |
| 932) | formyl | methyl | 4-trifluoromethylphenyl | 2,4-difluorophenyl | |
| 933) | formyl | methyl | 4-trifluoromethylphenyl | 4-chlorophenyl | |
| 934) | formyl | methyl | 4-trifluoromethylphenyl | 3-chlorophenyl | |
| 935) | formyl | methyl | 4-trifluoromethylphenyl | 2-chlorophenyl | |
| 936) | formyl | methyl | 4-trifluoromethylphenyl | 4-chloro-2-methoxyphenyl | |
| 937) | formyl | methyl | 4-trifluoromethylphenyl | 4-trifluoromethylphenyl | |
| 938) | formyl | methyl | 4-trifluoromethylphenyl | 2-trifluoromethylphenyl | |
| 939) | formyl | methyl | 4-trifluoromethylphenyl | 3-trifluoromethylphenyl | |
| 940) | formyl | methyl | 4-trifluoromethylphenyl | 4-(trifluoromethoxy)phenyl | |
| 941) | formyl | methyl | 4-trifluoromethylphenyl | 3-(trifluoromethoxy)phenyl | |
| 942) | formyl | methyl | 4-trifluoromethylphenyl | 4-(difluoromethoxy)phenyl | |
| 943) | formyl | methyl | 4-trifluoromethylphenyl | 3-(difluoromethoxy)phenyl | |
| 944) | formyl | methyl | 4-trifluoromethylphenyl | 4-cyanophenyl | |
| 945) | formyl | methyl | 3,4-dichlorophenyl | 4-fluorophenyl | |
| 946) | formyl | methyl | 3,4-(formylenedioxy)phenyl | phenyl | |
| 947) | formyl | methyl | 3-trifluoromethylphenyl | phenyl | |
| 948) | formyl | methyl | 3-trifluoromethylphenyl | 4-ethylphenyl | |
| 949) | formyl | methyl | 3-trifluoromethylphenyl | 4-formylphenyl | |
| 950) | formyl | methyl | 3-trifluoromethylphenyl | 2-formylphenyl | |
| 951) | formyl | methyl | 3-trifluoromethylphenyl | 3-formylphenyl | |
| 952) | formyl | methyl | 3-trifluoromethylphenyl | 4-fluorophenyl | |
| 953) | formyl | methyl | 3-trifluoromethylphenyl | 2,4-difluorophenyl | |
| 954) | formyl | methyl | 3-trifluoromethylphenyl | 4-chlorophenyl | |
| 955) | formyl | methyl | 3-trifluoromethylphenyl | 3-chlorophenyl | |
| 956) | formyl | methyl | 3-trifluoroethylphenyl | 2-chlorophenyl | |
| 957) | formyl | methyl | 3-trifluoromethylphenyl | 4-chloro-2-methoxyphenyl | |
| 958) | formyl | methyl | 3-trifluoromethylphenyl | 4-trifluoromethylphenyl | |
| 959) | formyl | methyl | 3-trifluoromethylphenyl | 2-trifluoromethylphenyl | |
| 960) | formyl | methyl | 3-trifluoromethylphenyl | 3-trifluoromethylphenyl | |
| 961) | formyl | methyl | 3-trifluoromethylphenyl | 4-(trifluoromethoxy)phenyl | |
| 962) | formyl | methyl | 3-trifluoromethylphenyl | 3-(trifluoromethoxy)phenyl | |
| 963) | formyl | methyl | 3-trifluoromethylphenyl | 4-(difluoromethoxy)phenyl | |
| 964) | formyl | methyl | 3-trifluoromethylphenyl | 3-(difluoromethoxy)phenyl | |
| 965) | formyl | methyl | 3-trifluoromethylphenyl | 4-cyanophenyl | |
| 966) | formyl | methyl | 4-formylphenyl | phenyl | |
| 967) | formyl | methyl | 4-methoxyphenyl | phenyl | |
| 968) | formyl | methyl | 4-chlorophenyl | phenyl | |
| 969) | H | H | 2-chloro-6-fluorophenyl | phenyl | m.p. 139–141° C. |
| 970) | H | H | 2-chloro-6-fluorophenyl | 4-fluorophenyl | m.p. 73–75° C. |
| 971) | H | H | phenyl | 4-cyanophenyl | m.p. 174–176° C. |
| 972) | H | H | phenyl | 4-bromophenyl | m.p. 190–191° C. |
| 973) | H | H | phenyl | 4-iodophenyl | m.p. 194–196° C. |

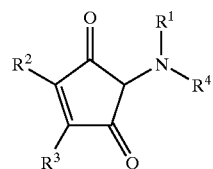

TABLE 1-continued

[Structure: cyclopentene-dione with R¹, R², R³, R⁴ and N substituents]

| No. | R¹ | R² | R³ | R⁴ | Phys. Data |
|---|---|---|---|---|---|
| 974) | acetyl | H | phenyl | phenyl | m.p. 147–148° C. |
| 975) | formyl | H | phenyl | phenyl | m.p. 140–141° C. |
| 976) | H | H | 4-phenylphenyl | 4-fluorophenyl | m.p. 231–233° C. |
| 977) | H | H | 2,6-dichloro-phenyl | phenyl | m.p. 131–132° C. |
| 978) | H | H | 4-phenylphenyl | phenyl | m.p. 247–249° C. |
| 979) | methyl | H | 4-phenylphenyl | phenyl | m.p. 183–185° C. |
| 980) | acetyl | H | 4-chlorophenyl | phenyl | m.p. 129–131° C. |

The compounds of the formula I can preferably be prepared according to the following reaction scheme:

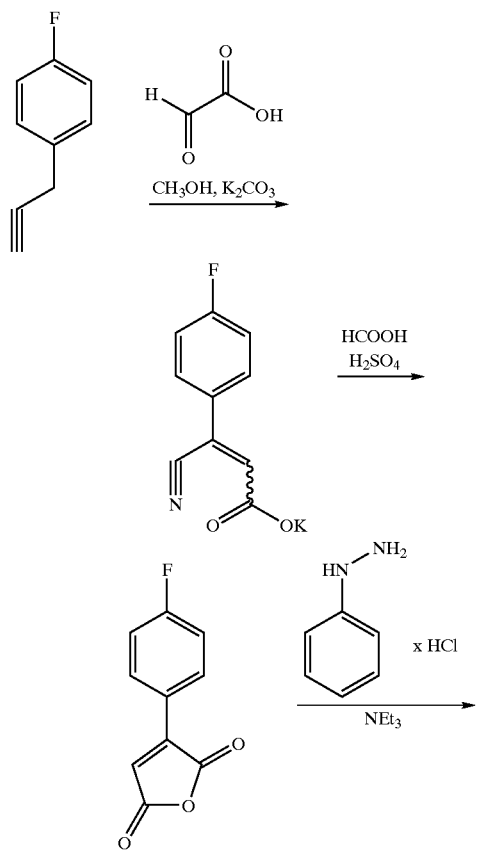

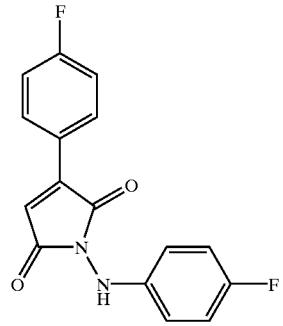

The compounds of the formula II listed in Table 2 below are novel compounds:

TABLE 2

(II)

[Structure: maleimide with R¹, R², Rᵃ, Rᵇ substituents]

| No. | R¹ | R² | Rᵃ | Rᵇ |
|---|---|---|---|---|
| 1) | H | H | phenyl | 4-isopropylphenyl |
| 2) | H | H | phenyl | 2,3,5,6-tetrafluorophenyl |
| 3) | H | H | phenyl | 4-trifluoromethylphenyl |
| 4) | H | H | phenyl | 4-chlorophenyl |
| 5) | H | H | phenyl | 3-chlorophenyl |
| 6) | H | H | phenyl | 2-chlorophenyl |
| 7) | H | H | phenyl | 3,5-dichlorophenyl |
| 8) | H | H | phenyl | 4-(trifluoromethoxy)phenyl |
| 9) | H | H | 4-chlorophenyl | 4-trifluoromethylphenyl |
| 10) | H | H | 4-chlorophenyl | 2-chlorophenyl |
| 11) | H | H | 4-chlorophenyl | 3-chlorophenyl |
| 12) | H | H | 4-fluorophenyl | phenyl |
| 13) | H | H | 4-fluorophenyl | 4-fluorophenyl |
| 14) | H | H | 3,4-dichloro-phenyl | 4-fluorophenyl |
| 15) | methyl | H | phenyl | phenyl |
| 16) | formyl | H | 4-chlorophenyl | phenyl |
| 17) | H | H | 2-chloro-6-fluorophenyl | phenyl |
| 18) | H | H | 2-chloro-6-fluorophenyl | 4-fluorophenyl |
| 19) | H | H | phenyl | 4-cyanophenyl |
| 20) | H | H | phenyl | 4-bromophenyl |
| 21) | H | H | phenyl | 4-iodophenyl |
| 22) | acetyl | H | phenyl | phenyl |
| 23) | formyl | H | phenyl | phenyl |
| 24) | H | H | 4-phenylphenyl | 4-fluorophenyl |
| 25) | H | H | 2,6-dichloro-phenyl | phenyl |
| 26) | H | H | 4-phenylphenyl | phenyl |
| 27) | methyl | H | 4-phenylphenyl | phenyl |
| 28) | acetyl | H | 4-chlorophenyl | phenyl |

Compounds of the formula II are in particular those in which $R^1$ is a hydrogen atom or a $C_1$–$C_4$-alkyl group or a formyl group (—CHO). Preference is furthermore given to compounds II in which the radicals $R^2$, $R^a$ and $R^b$ independently of one another have the following meanings:

$R^2$ is hydrogen;

$R^a$ is phenyl which may be mono- or polysubstituted, preferably mono- or disubstituted, by halogen or by a phenyl group which for its part may also be substituted by halogen or $C_1$–$C_4$-haloalky, $C_1$–$C_4$-haloalkoxy.

$R^b$ is phenyl which may be mono- or polysubstituted, preferably mono- to tetrasubstituted, by halogen, $C_1$–$C_6$-alkyl, $C_1$–$C_4$-haloalkyl, $C_1$–$C_4$-haloalkoxy.

In this context, the radicals $R^1$, $R^a$ and $R^b$ in the case of the compounds II have, for example, the following meanings:

$R^1$: hydrogen, methyl, formyl;
$R^2$: hydrogen;
$R^a$: phenyl, 4-chlorophenyl, 4-fluorophenyl, 3,4-dichlorophenyl, 2-chloro-6-fluorophenyl, 4-phenylphenyl, 2,6-dichlorophenyl or 2-chlorophenyl.
$R^b$: 4-isopropylphenyl, 2,3,5,6-tetrafluorophenyl, 4-trifluoromethylphenyl, 4-chlorophenyl, 3-chlorophenyl, 2-chlorophenyl, 3,5-dichlorophenyl, 4-(trifluoromethoxy)phenyl, 4-trifluoromethylphenyl, phenyl, 4-fluorophenyl, 4-cyanophenyl, 4-bromophenyl, 4-iodophenyl.

The compounds I have an excellent fungicidal activity. This is true, in particular, for the compounds Nos. 1, 13, 14, 17, 23, 26, 30, 31, 34, 35, 36, 38, 43, 45, 46, 51, 56, 969, 970, 971, 30 972, 973 and 977 listed in Table 1. Particularly preferred compounds are the following: Nos. 13, 14, 23, 26, 31, 35, 36, 38, 46, 56, 969, 970, 971, 972, 973 and 977 listed in table 1. Particularly preferred compounds are the following: Nos. 13, 14, 23, 26, 31, 35, 36, 38, 46, 56, 969, 970, 971, 972 and 973.

Normally, the plants are sprayed or dusted with the active compounds, or the seeds of the plants are treated with the active compounds.

The formulations (fungicidal compositions or agrochemical compositions) are prepared in a known manner, e.g. by extending the active compound with solvents and/or carriers, if desired using emulsifiers and dispersants, it also being possible to use other organic solvents as auxiliary solvents if water is used as diluent. Suitable auxiliaries are essentially: solvents, such as aromatics (e.g. xylene), chlorinated aromatics (e.g. chlorobenzenes), paraffins (e.g. mineral oil fractions), alcohols (e.g. methanol, butanol), ketones (e.g. cyclohexanone), amines (e.g. ethanolamine, dimethylformamide) and water; carriers, such as ground natural minerals (e.g. kaolins, clays, talc, chalk) and ground synthetic minerals (e.g. highly-disperse silica, silicates); emulsifiers, such as non-ionic and anionic emulsifiers (e.g. polyoxyethylene fatty alcohol ethers, alkylsulfonates and arylsulfonates) and dispersants, such as lignosulfite waste liquors and methylcellulose.

Suitable surfactants are the alkali metal salts, alkaline earth metal salts and ammonium salts of aromatic sulfonic acids, e.g. ligno-, phenol-, naphthalene- and dibutylnaphthalenesulfonic acid, or of fatty acids, alkyl- and alkylarylsulfonates, alkyl, lauryl ether and fatty alcohol sulfates, and salts of sulfated hexa-, hepta- and octadecanols, and also of fatty alcohol glycol ether, condensates of sulfonated naphthalene and of its derivatives with formaldehyde, condensates of naphthalene or of the naphthalenesulfonic acids with phenol and formaldehyde, polyoxyethylene octylphenol ether, ethoxylated isocctyl-, octyl- or nonylphenol, alkylphenol polyglycol ether, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methycellulose.

Powders, materials for spreading and dusts can be prepared by mixing or grinding the active ingredients together with a solid carrier.

Granules, e.g. coated granules, impregnated granules and homogeneous granules, can be prepared by binding the active compounds to solid carriers. Solid carriers are mineral earths, such as silica gel, silicic acids, silicates, talc, kaolin, limestone, lime, chalk, bole, loess, clay, dolomite, diatomaceous earth, calcium sulfate, magnesium sulfate, magnesium oxide, ground synthetic materials, fertilizers, such as ammonium sulfate, ammonium phosphate, ammonium nitrate, ureas, and products of vegetable origin, such as cereal meal, ureas, and meal, wood meal and nutshell meal, cellulose powders, or other solid carriers.

Examples of such preparations are:

I. a solution of 90 parts by weight of a compound I according to the invention and 10 parts by weight of N-methyl-pyrrolidone which is suitable for use in the form of microdrops;

II. a mixture of 10 parts by weight of a compound I according to the invention, 70 parts by weight of xylene, 10 parts by weight of the adduct of 8 to 10 mol of ethylene oxide to 1 mol of oleic acid N-monoethanolamide, 5 parts by weight of calcium dodecylbenzesulfonate, 5 parts by weight of the adduct of 40 mol of ethylene oxide to 1 mol of castor oil; a dispersion is obtained by finely distributing the solution in water.

III. an aqueous dispersion of 10 parts by weight of a compound I according to the invention, 40 parts by weight of cyclohexanone, 30 parts by weight of isobutanol, 20 parts by weight of the adduct of 40 mol of ethylene oxide to 1 mol of castor oil;

IV. an aqueous dispersion of 10 parts by weight of a compound I according to the invention, 25 parts by weight of cyclohexanol, 55 parts by weight of a mineral oil fraction of boiling point 210 to 280° C. and 10 parts by weight of the adduct of 40 mol of ethylene oxide to 1 mol of castor oil;

V. a mixture, ground in a hammer mill, of 80 parts by weight of a compound I according to the invention, which is preferably in solid form, 3 parts by weight of sodium diisobutylnaphthalene-2-sulfonate, 10 parts by weight of a sodium lignosulfonate from a sulfite waste liquor and 7 parts by weight of pulverulent silica gel; a spray mixture is obtained by finely distributing the mixture in water;

VI. an intimate mixture of 3 parts by weight of a compound I according to the invention and 97 parts by weight of finely divided kaolin; this dust comprises 3% by weight of active compound;

VII. an intimate mixture of 30 parts by weight of a compound I according to the invention, 62 parts by weight of pulverulent silica gel and 8 parts by weight of paraffin oil which has been sprayed onto the surface of this silica gel; this preparation imparts good adhesion properties to the active compound;

VIII. a stable aqueous dispersion of 40 parts by weight of a compound I according to the invention, 10 parts by weight of the sodium salt of a phenolsulfonic acid/urea/formaldehyde condensate, 2 parts by weight of silica gel and 48 parts by weight of water, which can be diluted further;

IX. a stable oily dispersion of 20 parts by weight of a compound I according to the invention, 2 parts by weight of calcium dodecylbenzenesulfonate, 8 parts by weight of fatty alcohol polyglycol ether, 20 parts by weight of the sodium salt of a phenolsulfonic acid/urea/formaldehyde condesate and 50 parts by weight of a paraffinic mineral oil.

The active compounds of the formula I are distinguished by an outstanding activity against a broad spectrum of phytopathogenic fungi, in particular from the classes of the Ascomycetes, Deuteromycetes, Phycomycetes and Basidiomycetes. Some of them act systemically, and they can therefore also be employed as foliar- and soil-acting fungicides.

They are particlarly important for the control of a large number of fungi on a variety of crop plants, such as wheat, rye, barley, oats, rice, maize, grass, cotton, soya, coffee, sugar cane, grape vine, fruit-bearing species, ornamentals and vegetables, such as cucumbers, beans and cucurbits, and on the seed of these plants.

The compounds are applied by treating the fungi or the seed, plants, materials or soil to be protected against fungal infection with a fungicidally active amount of the active compounds. They are applied before or after infection of the materials, plants or seeds with the fungi.

Specifically, the novel compounds are suitable for controlling the following plant diseases: *Erysiphe graminis* (powdery mildew) in cereals, *Erysiphe cichoracearum* and *Sphaerotheca fuliginea* in cucurbits, *Podosphaera leucotricha* in apples, *Uncinula necator* in grapevine, Puccinia species in cereals, Rhizoctonia species in cotton and lawn, Ustilago species in cereals and sugar cane, *Venturia inaegualis* (scab) in apples, Helminthosporium species in cereals, *Septoria nodorum* in wheat, *Botrytis cinerea* (gray mold) in strawberries, grapevine, ornamentals and vegetables, *Cercospora arachidicola* in groundnuts, *Pseudocercosporella herpotrichoides* in wheat and barley, *Pyricularia oryzae* in rice, *Phytophthora infestans* in potatoes and tomatoes, Fusarium and Verticillium species in a variety of plants, *Plasmopara viticola* in grapevine and Alternaria species in vegetables and fruit.

The active compounds of the formula I can be present either in free from or in the form of their agriculturally utilizable or environmentally compatible salts. Such salts are, for example, acid addition salts with inorganic or organic acids, for example hydrochloric acid, sulfuric acid, acetic acid, and other acids.

The active compounds of the formula I can also be employed in the protection of materials (protection of wood), e.g. against *Paecilomyces variotii*.

In general, the fungicidal compositions comprise of from 0.1 to 95, preferably from 0.5 to 90, % by weight of active compound.

Depending on the nature of the desired effect, the rates of application are between 0.025 and 2, preferably 0.1 to 1, kg of active compound per ha.

In the treatment of seed, amounts of 0.001 to 50 g, preferably 0.01 to 10 g, of active compound are generally required per kilogram of seed.

The compositions according to the invention can also be present in the application form as fungicides together with other active compounds, e.g. herbicides, insecticides, growth regulators and fungicides, or else with fertilizers.

In many cases, mixing them with other fungicidally active compounds results in a widened fungicidal spectrum of action. In particular when used in combination with other fungicidally active compounds, the active compounds of the formula I reduce the risk of development of resistance compared to the use of the individual active compounds.

If the crop plants or the seeds are treated with combination preparations of active compounds of the formula I and other fungicidally active compounds, this application can be carried out simultaneously or successively. If the active compounds of the formula I are used simultaneously with other fungicides, this is advantageously carried out by preparing an agrochemical mixture of the two active compounds, which mixture is used in a customary manner for treating the crop plants or the seeds. If the active compounds are applied successively, this is advantageously carried out by using the individual active compounds either within a short period of time or in intervals of several days or weeks.

The overall frequency of the treatment of plants or of seeds with fungicides can be reduced by this combined application.

For the purpose of the present invention, the term "combination preparation" is to be understood as meaning, in principle, all agrochemical composition which comprise active compounds of the formula I or II and one or more active compounds, in particular those having fungicidal action, for example in the form of customary agrochemical mixtures. Furthermore, the term "combination preparations" also includes those agrochemical preparations which comprise active compounds of the formula I and furthermore a note that these active compounds are suitable for combined application with other active compounds in the agricultural sector. Such a note may be present, for example, in the form of a label on the packaging on the commercial product or on the container containing the active compound of the formula I and/or the agrochemical composition which comprises an active compound of the formula I. Alternatively, it is also possible for other agrochemical products to contain corresponding notes concerning the combined application with compounds of the formula I or II. In this context, such products are likewise combination preparations which are suitable for use in combination with active compounds of the formula I and/or II.

The following list of fungicides together with which the compounds according to the invention can be used is intended to illustrate possible combinations, but not to impose any limitation:

sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N-propylenebisdithiocarbamate), zinc (N,N-propylenebisdithiocarbamate), N,N-polypropylenebis (thiocarbamoyl) disulfide;

nitro derivatives, such as dinitro-(1-methylheptyl)phenyl crotonate, 2-sec-butyl-4,6-dinitrophenyl-3,3-dimethylacrylate, 2-sec-butyl-4,6-dinitrophenyl isopropyl carbonate, diisopropyl 5-nitro-isophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithio-anthraquinone, 2-thio-1,3-dithiolo-[4,5-b]-quinoxaline, methyl 1-(butylcarbamoyl)-2-benzimidazolecarbamate, 2-methoxycarbonylaminobenzimidazole, 2-(fur-2-yl) benzimidazole, 2-(thiazol-4-yl )benzimidazole, N-(1,1, 2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfuric diamide, 5-ethoxy-3-trichloromethyl-1, 2,3-thiadiazole, 2-thiocyanomethylthiobenzothiazole, 1,4-dichloro-2,5-dimethoxybenzene, 4-(2- chlorophenylhydrazono)-3-methyl-5-isoxazolone, pyridine 2-thion-1-oxide, 8-hydroxyquinoline and its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanlilide, 2,4,5-trimethylfuran-3-carboxanilide cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloromethyl acetal, piperazine-1,4-diylbis(1-(2,2,2-trichloroethyl)formamide, 1-(3,4-dichloroanilino)-1-formylamino-2,2,2-trichloroethane, 2,6-dimethyl-N-tridecylmorpholine and its salts, 2,6-dimethyl-N-cyclododecylmorpholine and its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-ylethyl]-1H-1,2 4-triazole, 1-[2-(2,4-dichlorophenyl)-4-n-Proply-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, (2-chlorophenyl)-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, [2-(4-chlorophenyl)ethyl]-(1,1-dimethylethyl)-1H-1,2,4-triazol-1-ethanol, 1-[3-(2-chlorophenyl)-1-(4-fluorophenyl)oxiran-2-ylmethyl]-1H-1,2,4-triazole, and various fungicides, such as dodecylguanidine acetate, 3-[3-(3,5-dimethyl-2-oxycyclohexyl)-2-hydroxyethyl)]glutarimide, hexachlorobenzene, methyl N-(2,6-dimethylphenyl)-N-(2-furoyl)-DL-alaninate, methyl N-(2,6-dimethylphenyl)-N-(2'-methoxyacetyl)-D,L-alaninate, N-(2,6-dimethylphenyl)-N-chloroacetyl-D,L-2-amino-butyrolactone, methyl N-(2,6-dimethylphenyl)-N-(phenylacetyl)-DL-alaninate, 5-methyl-5-vinyl-3-(3,5-dichlorophenyl)-2,4-dioxo-1,3-oxazolidine, 3-(3,5-dichlorophenyl)-5-methyl-5-methoxy-methyl-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano- [N-(ethylaminocarbonyl)-2-methoximino]acetamide, 1-[2-(2,4-dichlorophenyl) pentyl]-1H-1,2,4-triazole, 2,4-difluoro-a-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis(4-fluorophenyl) methylsilyl)-methyl)-1H-1,2,4-triazole, strobilurins, such as methyl E-methoximino-[α-(o-tolyloxy)-o-tolyl]acetate, methyl E-2-{2-[6-(2-cyanophenoxy)pyrimidin-4-yloxy]phenyl}-3-methoxyacrylate, methyl-E-methoximino-[α-(2-phenoxyphenyl)]acetamide, N-methyl-E-methoximino-[α-(2,5-dimethyloxy)-o-tolyl]acetamide, anilinopyrimidines, such as N-(4,6-dimethylpyrimidin-2-yl)aniline, N-[4-methyl-6-(1-propinyl)pyrimidin-2-yl] aniline, N-(4-methyl-6-cyclopropylpyrimidin-2-yl) aniline, phenylpyrroles, such as 4-(2,2difluoro-1,3-benzodioxol-4-yl)pyrrole-3-carbonitrile, cinnamamides, such as 3-(4-chlorophenyl)-3-(3,4-dimethoxyphenyl)-acryloylmorpholide.

The invention is illustrated in more detail by the working examples below:

EXAMPLE 1

1-Anilino-3-(3,4-dichlorophenyl)-pyrrole-2,5-dione
(Table 1, No. 12)

a) Potassium 3-Cyano-3-(3,4-dichlorophenyl)acrylate 18.6g (0.1 mol) of (3,4-dichlorophenyl)acetonitrile and 35 g (0.25 mol) of potassium carbonate were initially charged in 200 ml of methanol and admixed with 22.2 g (0.15 mol) of 50% strength agueous glyoxylic acid, and the mixture was stirred at room temperature for 5 h. The residue was filtered off, washed with methylene chloride, stirred with 1 l of water at room temperature overnight and filtered off, and the precipitated product was washed with water and dried. Yield 26.2 g, m.p. 235–238° C.

b) (3,4-Dichlorophenyl)furan-2,5-dione 25.8 g (92 mmol) of potassium 3-cyano-3-(3,4-dichlorophenyl)acrylate were dissolved in 200 ml of 88% strength formic acid and admixed dropwise with 15 ml of concentrated sulfuric acid. The mixed was then heated under reflux for 3 h, poured at 90° C. into 2.5 l of water and stirred for 1 h, and the product was filtered off, washed with water and dried. Yield: 18.9 g, m.p. 112° C.

c) 1-Anilino-3-(3,4-dichlorophenyl)pyrrole-2,5-dione 2.43 g (10 mmol) of -(3,4-dichlorophenyl)furan-2,5-dione and 1.08 g (10 mmol) of phenyl hydrazine in 50 ml of glacial acetic acid were boiled under ref lux for 5 h. The mixture was cooled and the product was then filtered off and washed first with glacial acetic acid and subquently with pentane. Yield: 1.8 g of a crystalline solid, m.p. 208–210° C.

EXAMPLE 2

Activity Against *Phytophthora infestans* on Tomatoes

Leaves of potted plants cv. "Große Fleischtomate" were sprayed to runoff point with an aqueous suspension which had been prepared from a stock solution comprising 10% of active compound, 63% of cycbohexanone and 27% of emulsifier. The next day, the leaves were infected with an aqueous zoospore suspension of *Phytophthora infestans*. The plants were subsequently placed in a chamber saturated with water vapor, at 16–18° C. After 6 days, the late blight on the untreated but infected control plants had developed to such an extent that the infection could be determined visually in %.

| Active compound | % infection of the leaves after application of an aqueous preparation containing 250 ppm of active compound |
|---|---|
| Table 1. No. 1 | 15 |
| Table 1. No. 13 | 2 |
| Table 1. No. 17 | 5 |
| Table 1. No. 31 | 7 |
| Table 1. No. 34 | 5 |
| Table 1. No. 485 | 10 |
| Table 1. No. 969 | 3 |
| Table 1. NO. 971 | 3 |
| Table 1. No. 972 | 5 |
| Table 1. No. 973 | 8 |
| Untreated | 90 |

The table above shows that the damage caused by harmful fungi on the treated plants is considerably lower than on the untreated plants. Consequently, the active compounds according to the invention have good fungicidal activity. In particular, they have a protective effect against harmful fungi.

EXAMPLE 3

Activity Against *Plasmopara viticola*

Leaves of potted grapevines cv. "Müller-Thurgau" were sprayed to runoff point with an aqueous active compound preparation which had been prepared from a stock solution comprising 10% of active compound, 63% of cyclohexanone and 27% of emulsifier. To be able to assess the persistency of the substances, the plants were, after the spray coating had dried on, placed in a greenhouse for 7 days. Only then were the leaves inoculated with an aqueous zoospore suspension of *Plasmopara viticola*. The grapevines were then initially placed in a water-vapor-saturated chamber at 24° C. for 48 hours and subsequently in a greenhouse at 20–30° for 5 days. After this time, the plants were returned into a humid chamber for 16 hours to accelerate the sporangiophore eruption. The extent to which the disease had developed on the underside of the leaves was then determined visually.

| Active compound | % infection of the leaves after application of an aqueous preparation containing 250 ppm of active compound |
|---|---|
| Table 1. No. 1 | 5 |
| Table 1. No. 17 | 5 |
| Table 1. No. 30 | 15 |
| Table 1. No. 34 | 5 |
| Table 1. No. 43 | 15 |
| Table 1. No. 45 | 10 |
| Table 1. No. 51 | 15 |
| Table 1. No. 969 | 5 |
| Table 1. No. 971 | 10 |
| Table 1. No. 972 | 1 |
| Table 1. No. 973 | 1 |
| Table 1. No. 977 | 3 |
| Untreated | 85 |

We claim:

1. An agrochemical composition having fungicidal action, comprising a solvent and/or carrier and an effective amount of a compound of formula I

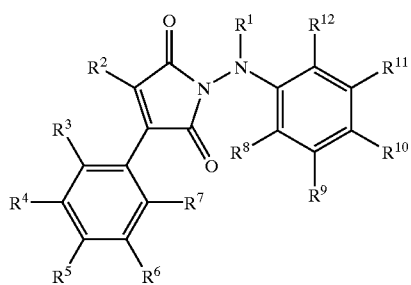

where:
   $R^1$ is formyl;
   $R^2$ is hydrogen, $C_1$–$C_6$-alkyl or $C_1$–$C_6$-haloalkyl;
   $R^3$ to $R^{12}$ are independently selected from the group consisting of hydrogen, halogen, $C_1$–$C_8$-cycloalkyl, $C_1$–$C_6$-alkyl, $C_1$–$C_6$-haloalkyl, $C_1$–$C_6$-alkoxy, $C_1$–$C_6$-haloalkoxy, $C_1$–$C_6$-alkysulfonyl, $C_1$–$C_6$-haloalkylsulfonyl, formyl, $C_1$–$C_6$-alkylcarbonyl, cyano, $C_1$–$C_6$-alkylthio and phenyl, wherein the pheny ring is unsubstituted or substituted by halogen, $C_1$–$C_6$-alkyl or $C_1$–$C_6$-haloalkyl, or an agriculturally useful salt thereof.

2. The composition defined in claim 1, where $R^2$ is hydrogen, $C_1$–$C_6$-alkyl or trifluoromethyl.

3. The composition defined in claim 2, where $R^2$ is hydrogen.

4. The composition defined in claim 1, where one or more of the radicals $R^3$ to $R^{12}$ are selected from the group consisting of fluorine, chlorine, methyl, ethyl, propyl, butyl, trifluoromethyl, difluoromethyl, trifluoromethoxy, difluoromethoxy, methoxy, methylthio and cyano, and the remaining radicals $R^3$ to $R^{12}$ are hydrogen.

5. The composition defined in claim 4, where four to nine of the radicals $R^3$ to $R^{12}$ are hydrogen.

6. The composition defined in claim 1, where two to five of the radicals $R^8$ to $R^{12}$ are hydrogen.

7. The composition defined in claim 6, where three or four of the radicals $R^8$ to $R^{12}$ are hydrogen.

8. The composition defined in claim 1, where two to five of the radicals $R^3$ to $R^7$ are hydrogen.

9. The composition defined in claim 8, where three or four of the radicals $R^3$ to $R^7$ are hydrogen.

10. The composition defined in claim 1, where at least two of the radicals $R^8$ to $R^{12}$ and at least two of the radicals $R^3$ to $R^7$ are hydrogen.

11. The composition defined in claim 1, where one, two or three of the radicals $R^3$ to $R^{12}$ are halogen, $C_1$–$C_6$-alkyl, $C_1$–$C_6$-haloalkyl, $C_1$–$C_6$-alkoxy or $C_1$–$C_6$-haloalkoxy.

12. The composition defined in claim 11, where the radicals $R^3$ to $R^{12}$ are selected from the group consisting of fluorine, chlorine, bromine, iodine, methyl, ethyl, propyl, butyl, trifluoromethyl, trifluoromethoxy and difluoromethoxy.

13. A compound of formula II

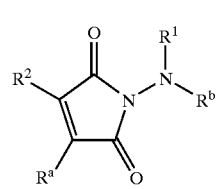

wherein
   $R^1$ is formyl;
   $R^2$ is hydrogen;
   $R^a$ is phenyl which is unsubstituted or substituted by halogen, or by a phenyl group which for its part is unsubstituted or substituted by halogen or $C_1$–$C_4$-alkyl;
   $R^b$ is phenyl which is unsubstituted or substituted by halogen, $C_1$–$C_6$-alkyl, $C_1$–$C_4$-haloalkyl, $C_1$–$C_4$-haloalkoxy.

14. A method for controlling harmful fungi, which comprises treating the harmful fungi, their habitat or plants, areas, materials or spaces to be kept free from the fungi with a fungicidally effective amount of a compound of formula I

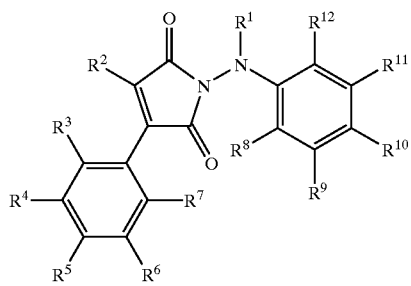

wherein

R¹ is hydrogen, $C_1$–$C_6$-alkyl, $C_1$–$C_6$-alkylcarbonyl, formyl or $C_1$–$C_6$-haloalkylcarbonyl;

R² is hydrogen, $C_1$–$C_6$-alkyl or $C_1$–$C_6$-haloalkyl;

R³ to R¹² are independently selected from the group consisting of hydrogen, halogen, $C_1$–$C_8$-cycloalkyl, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylsulfonyl, $C_1$–$C_6$-haloalkylsulfonyl, formyl, $C_1$–$C_6$-alkylcarbonyl, cyano, $C_1$–$C_6$-alkylthio and phenyl, wherein the phenyl ring is unsubstituted or substituted by halogen, $C_1$–$C_6$-alkyl or $C_1$–$C_6$-haloalkyl, or an agriculturally useful salt thereof.

15. An agrochemical composition comprising, as active components, the compound of formula I defined in claim 1, and at least one further fungicidally active compound.

16. The method of claim 14, wherein the compound of formula I is selected from the group consisting of 1-anilino-3-phenylpyrrole-2,5-dione, 1-anilino-3p-tolylpyrrole-2,5-dione, 1-(N-methylanilino)-3-p-tolylpyrrole-2,5-dione, 1-anilino-3-(3-chlorophenyl)pyrrole-2,5-dione, 1-anilino-3-(4-chlorophenyl)pyrrole-2,5-dione, 1-anilino-3-(4-bromophenyl)pyrrole-2,5-dione, 3-(4-chlorophenyl)-1-(N-methylanilino)pyrrole-2,5-dione, 1-(4-chloroanilino)-3-p-tolylpyrrole-2,5-dione, 3-(4-bromophenyl)-1-(4-methylanilino)pyrrole-2,5-dione, 1-(4-chloroanilino)-3-(4-chlorophenyl)pyrrole-2,5-dione, 1-anilino-3-(3,4-dichlorophenyl)pyrrole-2,5-dione, 3-(4-bromophenyl)-1-(4-methoxyanilino)pyrrole-2,5-dione, 3-(4-chlorophenyl)-1-(3,4-dichloroanilino)pyrrole-2,5-dione, 3-(4-methoxyphenyl)-1-(N-methylanilino)pyrrole-2,5-dione, 1-anilino-3-(4-methoxyphenyl)pyrrole-2,5-dione, 1-(4-chloroanilino)-3-(4-methoxyphenyl)pyrrole-2,5-dione, 1-(4-methoxyanilino)-3-(4-methoxyphenyl)pyrrole-2,5-dione, 1-(2-methoxyanilino)-3-(4-methoxyphenyl)pyrrole-2,5-dione, 1-(4-fluoroanilino)-3-(4-chlorophenyl)pyrrole-2,5-dione, 3-(4-chlorophenyl)-1-(4-methylanilino)pyrrole-2,5-dione, 1-(4-methylanilino)-3-phenylpyrrole-2,5-dione, 3-(4-chlorophenyl)-1-(2,4-dichloroanilino)pyrrole-2,5-dione, 1-(2,4-dichloroanilino)-3-phenylpyrrole-2,5-dione, and 1-(2,4-dichloroanilino)-3-(4-methoxyphenyl)pyrrole-2,5-dione.

17. The composition defined in claim 1, wherein

R² is hydrogen;

R³ to R⁷ are independently selected from the group consisting of hydrogen, halogen, and phenyl, wherein: the phenyl ring is unsubstituted or substituted by halogen or $C_1$–$C_4$-alkyl; and R⁸ to R¹² are independently selected from the group consisting of hydrogen, halogen, and phenyl, wherein the phenyl ring is unsubstituted or substituted by halogen, $C_1$–$C_6$-alkyl, $C_1$–$C_4$-haloalkyl or $C_1$–$C_4$-haloalkoxy.

18. The method of claim 14, wherein R¹ denotes formyl.

* * * * *

UNITED STATES PATENT AND TRADEMARK OFFICE
CERTIFICATE OF CORRECTION

PATENT NO.    : 6,476,061 B1
DATED         : November 5, 2002
INVENTOR(S)   : Rheinheimer et al.

It is certified that error appears in the above-identified patent and that said Letters Patent is hereby corrected as shown below:

Column 38,
Line 1, "pheny" should be -- phenyl --.

Column 39,
Line 33, "-3p-" should be -- -3-p- --.

Signed and Sealed this

Eighteenth Day of February, 2003

JAMES E. ROGAN
*Director of the United States Patent and Trademark Office*